US012383767B2

(12) United States Patent
Hale

(10) Patent No.: US 12,383,767 B2
(45) Date of Patent: *Aug. 12, 2025

(54) 3D STEREOSCOPIC CAMERA MONITORING SYSTEM AND METHOD OF CALIBRATING A CAMERA MONITORING SYSTEM FOR MONITORING A PATIENT IN A BORE OF A MEDICAL SYSTEM FOR RADIATION TREATMENT

(71) Applicant: Vision RT Limited, London (GB)

(72) Inventor: Gideon M. Hale, London (GB)

(73) Assignee: VISION RT LIMITED, London (GB)

( * ) Notice: Subject to any disclaimer, the term of this patent is extended or adjusted under 35 U.S.C. 154(b) by 267 days.

This patent is subject to a terminal disclaimer.

(21) Appl. No.: 18/106,858

(22) Filed: Feb. 7, 2023

(65) Prior Publication Data

US 2023/0181932 A1 Jun. 15, 2023

Related U.S. Application Data

(63) Continuation of application No. 16/387,271, filed on Apr. 17, 2019, now Pat. No. 11,612,762.

(30) Foreign Application Priority Data

Apr. 18, 2018 (GB) ...................................... 1806339
May 21, 2018 (GB) ...................................... 1808304

(51) Int. Cl.
*A61N 5/10* (2006.01)
*A61B 5/11* (2006.01)
(Continued)

(52) U.S. Cl.
CPC .......... *A61N 5/1049* (2013.01); *A61B 5/1128* (2013.01); *A61B 6/527* (2013.01);
(Continued)

(58) Field of Classification Search
CPC .......... A61N 2005/1059; A61N 5/1049; A61N 5/1075; A61B 2090/3618; A61B 5/1128;
(Continued)

(56) References Cited

U.S. PATENT DOCUMENTS 4,873,572 A 10/1989 Miyazaki et al.
11,163,169 B2 * 11/2021 Duckett, III ........... A61B 1/042
(Continued)

FOREIGN PATENT DOCUMENTS

EP 2 759 248 A2 7/2014
EP 3247458 11/2017
(Continued)

OTHER PUBLICATIONS

Extended European Search Report, dated Aug. 26, 2019, for European Application No. 19169458.7.

*Primary Examiner* — Behrooz M Senfi
(74) *Attorney, Agent, or Firm* — Birch, Stewart, Kolasch & Birch, LLP

(57) ABSTRACT

A camera monitoring system for a bore based medical apparatus is described, wherein the camera monitoring system comprises a first and a second image sensor mounted on opposing surfaces of a circuit board. The first image sensor is arranged to view an object from a first viewpoint via a first lens arrangement and a first mirror and the second image sensor is arranged to view the object from a second viewpoint via a second lens arrangement and a second mirror. By having the image sensors view an object via the mirrors, via the lens arrangements, the lens arrangements contribute to the effective separation of the first and second viewpoints enabling the size of the housing of the camera to be reduced. Furthermore, a method for calibrating a camera monitoring system in a bore based setup is described and also a
(Continued)

configuration of arranging a camera monitoring system in connection with a bore based medical apparatus.

17 Claims, 18 Drawing Sheets

(51) Int. Cl.
  *A61B 6/00* (2006.01)
  *G06T 7/00* (2017.01)
  *H04N 13/236* (2018.01)
  *H04N 13/246* (2018.01)
  *H04N 13/275* (2018.01)
  *A61B 90/00* (2016.01)

(52) U.S. Cl.
  CPC .......... *A61N 5/1075* (2013.01); *G06T 7/0014* (2013.01); *H04N 13/236* (2018.05); *H04N 13/246* (2018.05); *H04N 13/275* (2018.05); *A61B 2090/3618* (2016.02); *A61N 2005/1059* (2013.01); *G06T 2200/04* (2013.01)

(58) Field of Classification Search
  CPC ... A61B 6/527; G06T 2200/04; G06T 7/0014; H04N 13/236; H04N 13/239; H04N 13/246; H04N 13/25; H04N 13/254; H04N 13/275
  USPC .......................................................... 348/47
  See application file for complete search history.

(56) References Cited

U.S. PATENT DOCUMENTS

| | | | |
|---|---|---|---|
| 11,612,762 B2 * | 3/2023 | Hale | H04N 13/275 600/1 |
| 11,925,502 B2 * | 3/2024 | Amiri | A61B 6/5217 |
| 2003/0063292 A1 | 4/2003 | Mostafavi | |
| 2005/0267328 A1 | 12/2005 | Blumzvig et al. | |
| 2006/0079757 A1 | 4/2006 | Smith et al. | |
| 2011/0135190 A1 | 6/2011 | Maad | |
| 2016/0249984 A1 * | 9/2016 | Janssen | A61B 34/25 600/427 |
| 2016/0256712 A1 * | 9/2016 | Vahala | A61N 5/1039 |
| 2017/0319143 A1 | 11/2017 | Yu et al. | |
| 2018/0345040 A1 | 12/2018 | Meir et al. | |

FOREIGN PATENT DOCUMENTS

| | | | | |
|---|---|---|---|---|
| GB | 2530790 A | | 4/2016 | |
| JP | 2010191325 A | * | 9/2010 | ............ G03B 35/08 |
| JP | 2014-524290 A | | 9/2014 | |
| JP | 2015-515350 A | | 5/2015 | |
| JP | 2016-538901 A | | 12/2016 | |
| WO | WO 03/098913 A2 | | 11/2003 | |
| WO | WO 2012/149548 A2 | | 11/2012 | |
| WO | WO-2013025530 A1 | * | 2/2013 | ......... A61B 1/00009 |
| WO | WO 2017/178804 A1 | | 10/2017 | |

* cited by examiner

3D STEREOSCOPIC CAMERA MONITORING SYSTEM AND METHOD OF CALIBRATING A CAMERA MONITORING SYSTEM FOR MONITORING A PATIENT IN A BORE OF A MEDICAL SYSTEM FOR RADIATION TREATMENT

CROSS-REFERENCE TO RELATED APPLICATIONS

This application is a Continuation of copending application Ser. No. 16/387,271, filed on Apr. 17, 2019, which claims priority under 35 U.S.C. § 119(a) to Application No. 1806339.6, filed in Great Britain on Apr. 18, 2018, and Application No. 1808304.8, filed in Great Britain on May 21, 2018, all of which are hereby expressly incorporated by reference into the present application.

FIELD

The present disclosure concerns a 3D camera system. More specifically the present disclosure concerns a 3D camera system for monitoring the positioning and movement of patients during scanning and/or treatment. The invention is particularly suitable for use with radio therapy devices and computed tomography (CT) scanners and the like, where detection of patient movement or for example irregular breathing is important for successful treatment. Furthermore, the disclosure concerns a method of calibrating a patient monitoring system, constituted by the 3D camera system disclosed herein. The method is suitable for calibrating a patient monitoring system for monitoring the location of a patient with very high accuracy such as is required by a patient monitoring system for monitoring the positioning and location of a patient during radiotherapy.

BACKGROUND

Imaging technics, such as MR and CT imaging, within medical applications are generally used to diagnose patients within a wide area of diseases, especially to diagnose cancer and to plan a cancer treatment for the patient. The imaging techniques used for at least cancer diagnostics includes CT and MR scanning systems, from which imaging modalities a series of 3D diagnostic images are produced. The 3D image data are generally provided to a specialized doctor, who evaluates and analyses the images to evaluate and plan the subsequent treatment of the cancer. When a treatment plan has been set by a team of specialized clinician and doctors, the patient is exposed to radiotherapy treatment, which includes being positioned in a radiotherapy treatment apparatus having a radiation beam configured to focus the radiation beam at a specific target area of the body of the patient.

In general, radiotherapy consists of projecting a radiation beam onto a predetermined region of a patient's body so as to destroy or eliminate tumors existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful. Furthermore, during treatment a patient lies on a mechanical couch and is irradiated by a radiation source from a variety of different positions and angles. To ensure accurate application of radiation and avoid radiating adjacent tissue on which radiation beams would be harmful, the radiation source must be positioned with respect to the patient in order to irradiate the selected region with the highest possible accuracy and a patient should be made to adopt an identical pose when being irradiated to the pose adopted during the treatment planning phase and at each medical intervention.

Current radiotherapy treatment systems utilize a monitoring system which is configured to monitor patient movement occurring during treatment. Such tracking of the motion is in current system configured with a light projector, which projects light onto the surface of a patient to facilitate identification of corresponding portions of the surface of a patient captured from different viewpoints. Images of a patient are obtained and processed together with data identifying the relative locations of the cameras capturing the images relative to a treatment room iso-center, to identify 3D positions of a large number of points corresponding to points on the surface of a patient. Such data can be compared with data generated on a previous occasion and used to position a patient in a consistent manner or provide a warning when a patient moves out of position. Typically, such a comparison involves undertaking Procrustes analysis to determine a transformation which minimizes the differences in position between points on the surface of a patient identified by data generated based on live images and points on the surface of a patient identified by data generated on a previous occasion.

Current monitoring systems arranged in a radiotherapy treatment setup are configured to generate highly accurate (e.g. sub-millimeter) models of the surface of a patient. To do so, the monitoring system is calibrated in order to establish the relative locations and orientations of the image capture devices/cameras, as well as intrinsic internal camera parameters, such as any optical distortion caused by the optical design of the lens of each image detector/camera e.g. barrel, pincushion, and moustache distortion and de-centering/tangential distortion, and other internal parameters of the cameras/image capture devices (e.g. focal length, image center, aspect ratio skew, pixel spacing etc.). Once known, the internal camera parameters can be utilized to manipulate obtained images to obtain images free of distortion. 3D position measurements can then be determined by processing images obtained from different locations and deriving 3D positions from the images and the relative locations and orientations of the image capture devices/cameras.

Thus, current system exists which are able to accurately monitor and track patient while being positioned in a standard radiotherapy treatment room, where the couch may be configured to move in relation to a radiotherapy gantry setup.

However, as the design of radiotherapy, MR and CT systems continues to develop current system may be configured as a combined and fully integrated diagnostic and treatment system. Thus, within cancer diagnostic and treatment there is a general tendency towards combining these imaging and treatment modalities into a single bore based system, which can perform the imaging modalities needed for the diagnostic stages of cancer diagnostics as well as the radiotherapy treatment stage using a focused beam needed for the treatment stage. That is, as cancer is contained within a patient's body it is beneficial to provide imaging machines to obtain images of the internal anatomy of a patient. Increasingly such machines are being provided in the same room as radiation treatment apparatus enabling the internal anatomy of a patient to be reimaged during the course of treatment. Monitoring patient positioning with such machines again is challenging as a patient is moved between a treatment position and an imaging position during a treatment session. In other systems, the patient is lying on a couch inside the bore during both scanning and treatment.

In all stages, of diagnostic and treatment it is important to be able to monitor the patient, especially to monitor any potential motion of the patient while positioned on the couch during scanning and treatment. However, existing patient monitor camera systems are not configured and arranged in the treatment room in an optimal manner in view of providing a good view by the cameras, of the patient, when the patient is positioned inside the bore of the medical apparatus. Furthermore, current solutions for calibrating the different cameras used in a camera monitoring system for monitoring a patient needs to be sufficiently updated in view of the new integrated bore based medical apparatus's to be able to generate accurate monitoring of the patient during scanning and/or treatment of the patient.

Thus, it may with existing solutions be difficult to acquire accurate monitoring of the patient while being positioned inside the bore. Therefore, there is a need to provide solutions for monitoring camera setups, that addresses at least some of the above-mentioned problems. At least the present disclosure provides at least an alternative to the prior art.

SUMMARY

To ensure that sufficient monitoring of a patient lying in a bore based medical system is ensured, a camera monitoring system is provided for throughout this disclosure, Furthermore, a method for calibrating the camera monitoring system to enable an accurate monitoring of the patient is provided for.

In order to ensure that the camera monitoring system provides for a camera setup which is suitable for a bore based medical apparatus, it is desirable to reduce the physical size of 3D camera systems whilst maintaining the high levels of accuracy with which such systems can monitor the surface of a patient.

Thus, in accordance with one aspect of the present disclosure, there is provided a 3D camera which comprises a first and a second image sensor mounted on a circuit board, wherein the first and second image sensors are mounted on opposing surfaces of the circuit board. The circuit board is contained within a housing which also contains a first and a second mirror positioned within the housing so that the first image sensor is presented with a first view of an object to be imaged via the first mirror and second image sensor is presented with a second view of an object to be imaged via the second mirror. Mounting a first and a second image sensor on opposing surfaces of a circuit board in this manner and having the view objects to be imaged via a set of mirrors enables the overall size for the housing for a camera system to be reduced as the effective location of the image planes of the image sensors need not necessarily be located inside the housing.

Further, monitoring systems ordinarily require a lens for focusing images onto the image sensors. Conventionally, such lens arrangements have been orientated in front of image sensors aligned with the line of sight of the image sensors. By arranging image sensors to obtain images of objects to be viewed via mirrors, lenses can be arranged at an angle relative to the effective line of sight of the image sensors. In such a configuration, the length of the lens arrangement lies within the physical separation of the image planes of the image sensors and the size of the camera system can therefore be reduced.

The field of view of a camera system can be increased by providing multiple pairs of image sensors and associated lens arrangements and mirrors where the mirrors associated with different pairs of image detectors are angled relative to each other. In embodiments where three pairs of image sensors are provided in a camera, the mirrors associated with the image sensors can be provided on the surfaces of two rhomboidal trapezia to provide a wide angle of view.

Embodiments of the present invention may include a speckle projector for projecting a pattern of light onto the surface to be imaged. The projector may be such as a light projector projecting a pattern of light onto the surface to be imaged by the 3D cameras. Where image sensors are provided on opposing surfaces of a circuit board, a projector, preferably a light or speckle projector, may be positioned so as to be aligned with the circuit board. Such an arrangement may also reduce the overall size of the camera system. Further, aligning the speckle projector with the circuit board facilitates a symmetrical arrangement of the projected speckle pattern as viewed by the image sensors, which helps avoid a projected speckle pattern being more distorted when viewed by one of the image sensors compared with the other image sensor which facilitates the identification of corresponding portions of images of an object viewed from two different viewpoints.

The above described 3D camera could be incorporated in a patient monitoring system (i.e. a camera monitoring system) for monitoring patients undergoing radiotherapy. In such embodiments, the patient monitoring system could be arranged to generate a computer model of a portion of the surface of a patient and compare the generated model with a stored model and generate positioning instructions on the basis of such a comparison and/or provide a warning or halt treatment if it is detected that a patient is out of position by more than a threshold amount.

In another aspect of the disclosure it is important that the camera monitoring system is sufficiently calibrated so as to obtain accurate surface models of the patient during scanning and/or treatment.

Thus, in a second aspect of the disclosure there is provided a method of calibrating a patient monitoring system (i.e. a camera monitoring system) for monitoring the positioning of a patient, where the monitoring system is arranged to obtain images of a patient in a first location and a second location physically separated from the first location. A calibration object with a first set of calibration markings on a first portion and a second set of calibration markings on a second portion is provided and positioned so that the first set of calibration markings are visible in the vicinity of first location and the second set of calibration markings is visible in the vicinity of the second location. The patient monitoring system is then calibrated using obtained images of the positioned calibration object with the first and second sets of calibration markings positioned in the vicinity of the first and second positions.

The applicants have appreciated that the calibration of a patient positioning monitoring system can be simplified where a patient's position is required to be monitored in two locations having a fixed relationship to each other such as is the case with a treatment apparatus having a defined set up area and treatment area or a defined treatment area and imaging area. In such systems it is not necessary for a position monitoring system to monitor the motion of a patient between the two fixed locations, which would require a monitoring system to be calibrated to monitor a patient over a large area as they are moved between the two locations. Rather patient monitoring can instead be achieved by calibrating a patient monitoring system to monitor a patient only in the vicinity of the identified areas and any movement of a patient as they are transferred between those areas can be determined by comparing models generated from images of the patient as viewed in those specific areas provided that the monitoring system is calibrated in such a way that the model spaces of models of a patient in the first location and the second location are offset by an amount corresponding to the physical distance between the two locations. This can be achieved by imaging a calibration object having two sets of calibration markings where the spacing of the two sets of calibration markings corresponds to the physical spacing between the two locations the monitoring system is arranged to monitor. The calibration object can then be positioned with the calibration markings visible in those locations and the image of the markings can then be utilized to calibrate the system.

The monitoring system may comprise a plurality of 3D cameras, wherein at least one 3D camera is arranged to obtain images of objects in the first location and at least one 3D camera is arranged to obtain images of objects in the second location. In some embodiments the 3D cameras may comprise stereoscopic cameras. In other embodiments the 3D cameras may comprise 3D time of flight cameras or 3D cameras operable to obtain images of the projection of structured light onto the surface of an object being monitored.

The calibration object may comprise a calibration plate bearing a first and a second set of calibration markings each comprising an array of circular markings wherein the circular markings in the array are located in known positions relative to one another. In some embodiments the first and second sets of calibration markings may be angled relative to one another by a predetermined angle. The calibration markings may additionally comprise one or more lines arranged on the surface of the calibration object in a fixed relationship relative to the array of circular markings.

Positioning the calibration object may comprise utilizing a laser lighting system to highlight a position in space and aligning markings on the surface of the calibration object with the light projected by the laser lighting system. In such embodiments the laser lighting system may be arranged to highlight a position in space corresponding to: a treatment room iso-center of a radiotherapy treatment apparatus; a point identifying the center of a set up position for a patient undergoing radiotherapy treatment; or a point having a fixed relationship with an imaging apparatus for obtaining internal images of a patient undergoing radiotherapy.

Alternatively, or additionally, the calibration object may contain a set of radio opaque markers which may be utilized to assist with positioning the calibration object. In such embodiments positioning the calibration object may comprise irradiating and obtaining an irradiation image of the calibration object containing radio opaque markers and analyzing the obtained images to determine the relative positioning of the calibration object relative to an irradiation position such as a treatment room iso-center.

The images of the positioned calibration object may be used to determine the relative position and/or orientation of image planes of the cameras obtaining images of the object. The images of the positioned calibration object may also be used to determine internal characteristics of the cameras such as the presence of lens distortions.

Portions of the markings of the calibration object may identify the corners of squares and images of the positioned calibration object may be used to determine the relative position and/or orientation of image planes of the cameras obtaining images of the object relative to the center of such a square, the positioning of the calibration object being such to place the center of the square in a fixed location relative to a treatment room or imaging apparatus iso-center or a point in space highlighted by a laser lighting system.

Calibrating the monitoring system may enable the monitoring system to generate models of objects observed in the vicinity of the first location in a first model space and to generate models of objects observed in the vicinity of the second location in a second model space wherein the first and second model spaces are offset by a vector corresponding the physical distance between the first and second locations.

In some embodiments a patient may be rotated by a predefined angle between being positioned in the two locations where the patient is to be monitored. In such systems the processing of calibration images may be such to cause the system to generate surface models which are rotated by the same predefined angle to facilitate monitoring of a patient.

A further aspect of the present disclosure provides a calibration object for calibrating a patient positioning monitor operable to monitor the positioning of a patient relative to a first position and a second position separated by a fixed physical distance. The calibration object may comprise a first set of calibration markings and a second set of calibration markings positioned on the surface of the calibration object, the first and second set of physical markings being physically separated from one another by a distance corresponding to the distance between the first position and the second position at which monitoring by the patient positioning monitor occurs. In some embodiments the first set of calibration markings and second set of calibration markings may be rotated relative to one another by an angle. In some embodiments the calibration object may contain a set of radio-opaque markers.

Further details and additional embodiment falling within the scope of the disclosure, will be explained in the detailed description of the drawings in the following. Furthermore, it should be noted that throughout the disclosure, a projector of the system is defined as a speckle projector but it should be understood that any type of projector, projecting a pattern of light onto a surface could be used. Furthermore, the disclosure mentions that the processor of the camera monitoring system is configured to create 3D wire mesh models, but the skilled person would know that other suitable 3D model generation methods, such as for example point cloud models, could be used and would fall within the scope of the disclosure.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. The individual features of each aspect may each be combined with any or all features of the other aspects and embodiments. These and other aspects, features and/or technical effect will be apparent from and elucidated with reference to the illustrations described hereinafter in which:

DETAILED DESCRIPTION

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

An overview of the use of a patient positioning monitoring system for use with a radiotherapy treatment apparatus will first be described with reference to FIGS. 1-4.

Figure 1:
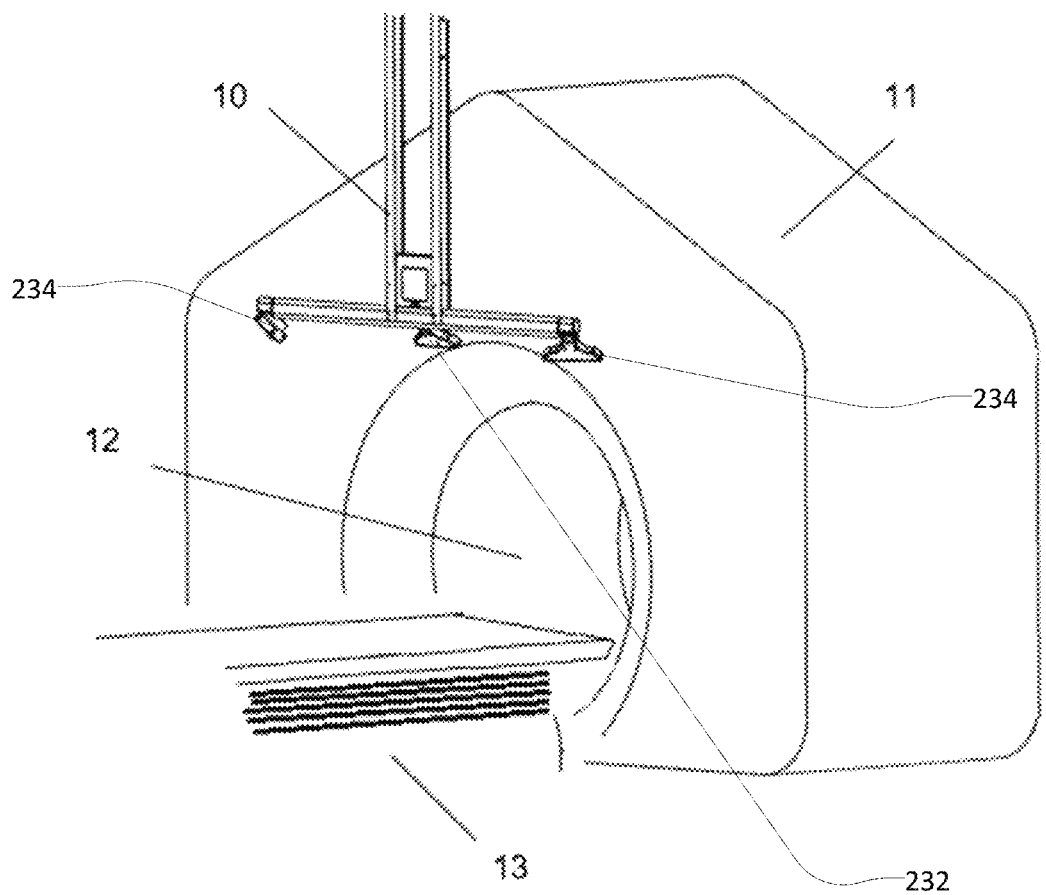
FIG. 1 is an illustrative schematic perspective view of a radiotherapy treatment apparatus and a patient monitoring system.

FIG. 1 is an exemplary illustration of a schematic perspective view of a patient monitoring system 10 in which a set of three stereoscopic cameras are provided suspended from the ceiling of a treatment room arranged to view a treatment apparatus 11 such as a linear accelerator for applying radiotherapy. In the illustrated example the treatment apparatus 11 is a treatment apparatus 11 which has a central bore 12. As will be described in greater detail the cameras of the monitoring system 10 are arranged to monitor a set up position directly in front of the treatment apparatus 11 and a treatment position centered on point in the center of the bore 12.

A mechanical couch 13 upon which a patient lies during treatment is provided adjacent the treatment apparatus 11. The treatment apparatus 11 and the mechanical couch 13 are arranged such that, under the control of a computer (not shown), the position of the mechanical couch 13 may be varied, laterally and vertically, longitudinally enabling a patient lying on the surface of the couch to be positioned in the middle of the bore 12 of the treatment apparatus 11.

Figure 2:
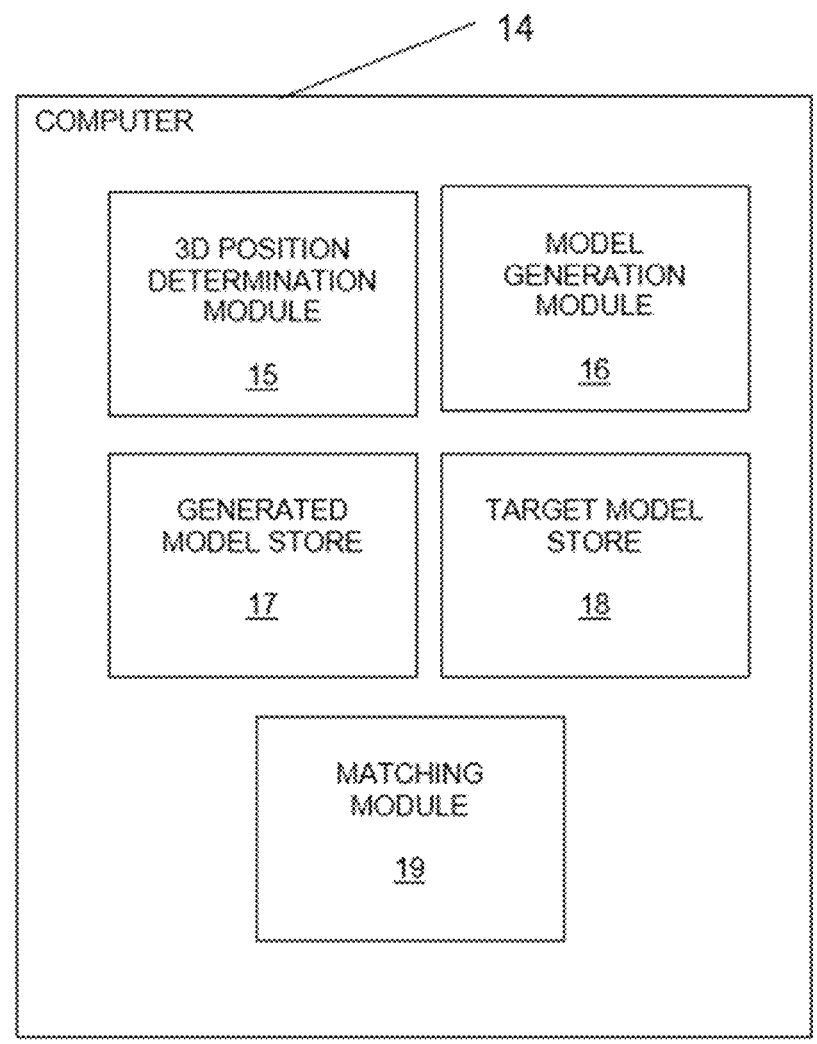
FIG. 2 is a schematic block diagram of a computer configured to process images of a patient being monitored.

FIG. 2 is a schematic block diagram of a computer 14 for processing images obtained by the patient monitoring system 10 of FIG. 1. In order for the computer to process images received from the stereoscopic cameras of the patient monitoring system 10, the computer 14 is configured by software into a number of functional modules 15-19. In this example, the functional modules 15-19 comprise: a 3D position determination module 15 for processing images of a patient received from the stereoscopic cameras to determine 3D position measurements of points on the surface of a patient; a model generation module 16 for processing position data generated by the 3D position determination module 15 and converting the data into a 3D wire mesh model of an imaged surface; a generated model store 17 for storing a 3D wire mesh model of an imaged surface; a target model store 18 for storing a previously generated 3D wire mesh model; and a matching module 19 for determining translations required to match a generated model with a target model.

In use, in this embodiment, the stereoscopic cameras of the monitoring system 10 obtain video images of a patient lying on the mechanical couch 13. These video images are passed to the computer 14 which processes the images of the patient together with data identifying the relative positions and orientations of the cameras and internal camera characteristics such as focal length, lens distortions etc. to generate a model of the surface of the patient which is stored in the generated model store 17. This generated model is compared with a stored model of the patient generated during earlier treatment sessions stored in the target model store 18. The matching module 19 then proceeds to determine translations required to match a generated model with a target model. When positioning a patient the difference between a current model surface and a target model surface obtained from an earlier session is identified and the positioning instructions necessary to align the surfaces determined and sent to the mechanical couch 13. If subsequently during treatment any deviation from an initial set up beyond a threshold can be identified, the computer sends instructions to the treatment apparatus 11 to cause treatment to be halted until the patient can be repositioned.

The construction of a stereoscopic camera 20 in accordance with an embodiment of the present invention will now be described in detail with reference to FIGS. 3-5.

Figure 3:
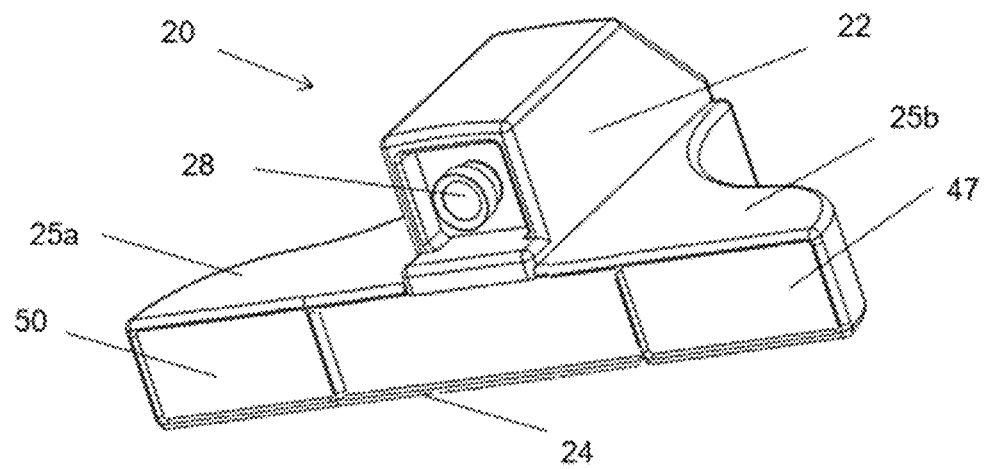
FIG. 3 is a schematic perspective view of the exterior of a camera system in accordance with an embodiment of the present disclosure.

Turning first to FIG. 3, which is a schematic perspective view of the exterior of a 3D stereoscopic camera 20 configured to record images of at least a patient lying on the couch during treatment, and from those images create a 3D surface model in the model generator. The stereoscopic camera 20 comprises a housing which in this embodiment consists of an upper portion 22 and a lower portion 24 where the lower portion 24 of the housing extends beneath and to either side of the upper portion 22 in the form of two wings 25a, 25b. In this embodiment, the upper portion 22 of the housing may extends 3 cm above the upper surface of lower portion 24 of the housing and has may have a width of 3.46 cm and a depth at its greatest point of 9.47 cm and the lower portion 24 of the housing has may have a height of 2.9 cm and a width of 20.4 cm at the greatest extent of the wings 25a, 25b.

The upper portion 22 of the housing is provided in the center of the camera 20 and defines a cavity which contains a speckle projector. As can best be seen in FIG. 4 which is a cut away cross sectional view of the stereoscopic camera 20, the speckle projector comprises: a light source 26, which in this embodiment comprises an infrared LED light source; a collimator 27; and a lens assembly 28. The light source 26 and collimator 27 are arranged to provide a collimated beam of infra-red light to the lens assembly 28. The lens assembly 28 may contains a pseudo random patterned transparency which partially blocks the light beam which causes light source 26, collimator 27 and the lens assembly 28 collectively to project a pseudo random pattern of infra-red light onto surfaces present in the vicinity of the camera 20.

Figure 4:
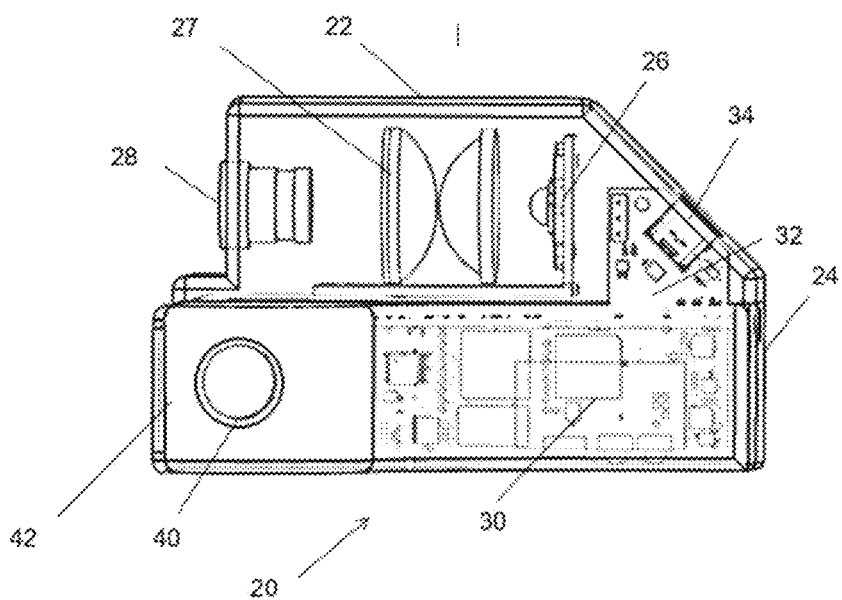
FIG. 4 is a cut away cross sectional view of the camera system of FIG. 3.
Figure 5:
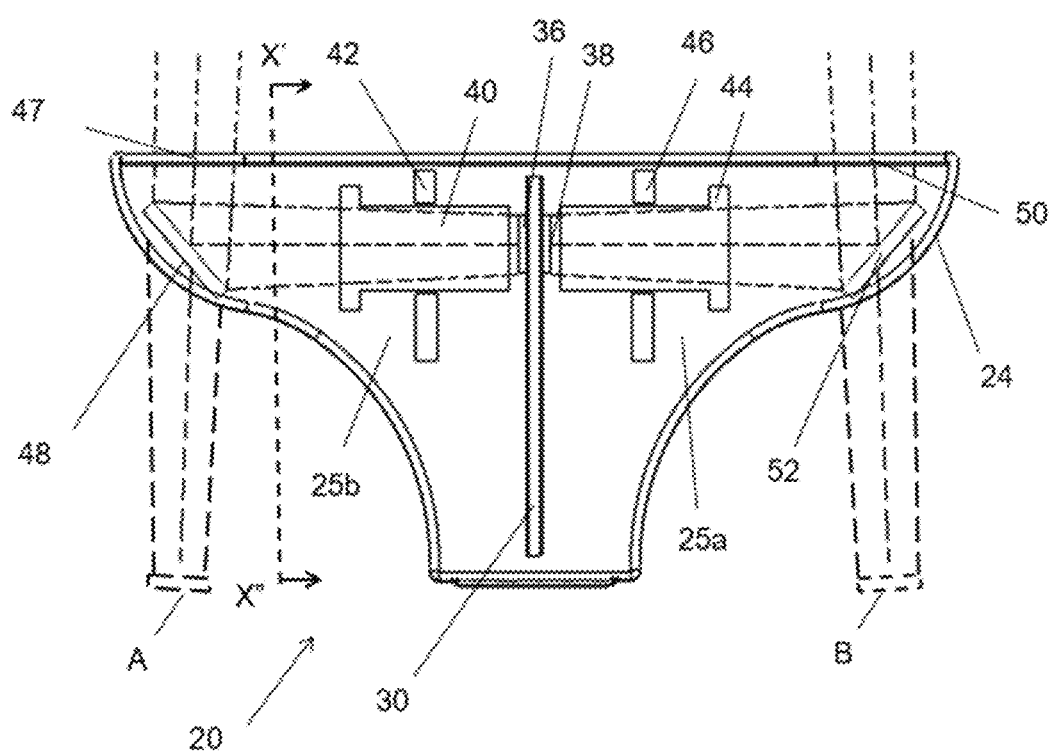
FIG. 5 is a cross sectional plan view of the lower portion of the camera system of FIG. 3.

FIG. 5 is a plan view of the lower portion 24 of the stereoscopic camera system of FIG. 3. The approximate location of the cut away side view of FIG. 4 is indicated by the line X'-X" in FIG. 5.

The housing is defined by an upper 22, and lower portion 24, and contains a circuit board 30 which is primarily located in the middle of the lower portion 22 of the housing 22 (see FIGS. 4 and 5). This circuit board 30 is positioned along the center line of the housing 22,24 at right angles to the front surface of the camera housing 22, 24 and extends along the entire depth of the lower portion 24 of the housing 24, effectively dividing the cavity enclosed by the lower portion 24 of the housing 24 into two equal parts.

In this embodiment a portion 32 of the circuit board 30 extends upwards into the upper part 22 of the housing 22 at the rear behind the speckle projector (see FIG. 4). In this embodiment a USB interface 34 for connecting the camera system to a power supply and for transmitting image data from the camera system is provided in this portion 32 of the circuit board 30. In other embodiments, if the circuit board 30 can be further reduced in size, this portion of the circuit board 30 can be omitted, in which case the total depth of the housing 22, 24 for the camera could be reduced so as to be limited to a size sufficient to accommodate the speckle projector in the upper portion 22 of the housing.

A first image sensor 36 and a second image sensor 38 which in this embodiment comprise may be configured as ⅓" CMV300 CMOS sensors are provided on the circuit board 30, at the other end of the circuit board 30 to the USB interface 34, with the first 36 and second 38 image sensors being provided on opposing surfaces of the circuit board 30 towards the front surface of the camera housing 22, 24 (see FIG. 5). It should be noted that the images sensors illustrated in this embodiment is provided on the each side of the same circuit board, however, it should be understood that the image sensors could also be mounted on two separate circuit boards. Thus, in the embodiment illustrated the image sensors are configured "back-to-back" via the same circuit board, however, they could also be arranged "back-to-back" via two separate circuit boards.

A first lens assembly 40 is mounted on a bracket 42 in front of the first image sensor 36 within one wing 25b of the lower portion 24 of the camera housing and a second lens assembly 44 is mounted on a second bracket 46 in front of the second image sensor 38 in the other wing 25a of the lower portion 24 of the camera housing, with the first 40 and second 44 lens assemblies extending perpendicularly away from opposite surfaces of the circuit board 30.

The first image sensor 36 is arranged to view surfaces onto which patterns of light are projected by the speckle projector through a window 47 at the front of the camera 20 via the first lens assembly 40 and an angled mirror 48 provided at one end of the lower portion of the housing 24. This window 47 appears on the right-hand-side of the device as shown in FIG. 3 and on the left-hand side of the device of the plan view of the device in FIG. 5.

The second image sensor 38 is arranged to view surfaces onto which patterns of light are projected by the speckle projector through a second window 50 via the second lens assembly 44 and a second angled mirror 52 provided at the opposite end of the lower portion of the housing 24. This second window 50 appears on the left-hand-side of the device as shown in FIG. 3 and the right-hand side of the device as shown in the plan view of FIG. 5.

In this embodiment the mirrors 48,52 included in the device are commercially available 15×25 mm mirrors such as COMAR 25 MP 16 mirrors with reflectance in the infra-red. The mirrors 48,52 are arranged within the lower portion 24 of the housing such that the distance between the center points of the mirrors is 15.154 cm. The center points of the mirrors 48,52 and the image sensors 36,38 are all aligned along an axis normal to the flat surface of the circuit board 30. Allowing for the thickness of the circuit board 30, which in this embodiment is 1.6 mm thick and the symmetrical arrangement of the mirrors 48,52 about the circuit board, this causes the center of each of the image sensors 36,38 to be 7.49 cm from the center of the mirror 48,52 which they view.

In this embodiment, the mirrors 48,52 are each angled at 43.5° relative to the surface of the circuit board 30. This arrangement of the image sensors 36,38 and the mirrors 48,52 causes the effective image planes of the image sensors 36,38, at the positions indicated as A and B in FIG. 5 with the image planes being located outside of housing 24, to be toed in relative to each other by 6° (i.e. double the 3° from 90° between the two mirrors since the relative changes in orientation impact both the angle of incidence and the angle of reflection onto and from the mirrors).

The above described camera design greatly reduces the size of the cameras required for patient monitoring compared with conventional designs. The total width of the camera system is largely dictated by the requirement that the image planes of the image sensors 36,38 need to be sufficiently separated so that images obtained by the image sensors 36,38 differ sufficiently to enable 3D position measurements to be made at the desired level of accuracy given the distances between a patient and a camera system and pixel density of the image sensors 36,38.

By providing image sensors 36,38 on opposing surfaces of a circuit board and having the image sensors view objects by viewing a reflection in a mirror 48,52 the above described design facilitates an arrangement where the lens assemblies 40,44 are positioned within the housing 24 and the lengths of the lens assemblies 40,44 also form part of the physical distance which acts to separate the effective positions A,B of the image planes of the image sensors 36,38.

The symmetrical arrangement of the circuit board 30, image sensors 36,38 and mirrors 48,52 also facilitates the alignment of the speckle projector with the center of device so that the projected patterns of light as viewed by the image sensors 36,38 are substantially similar without either sensor 36,38 viewing a projection which is more or less distorted that the other, which facilitates the identification of matching points in images obtained by the image sensors 36,38.

Figure 6:
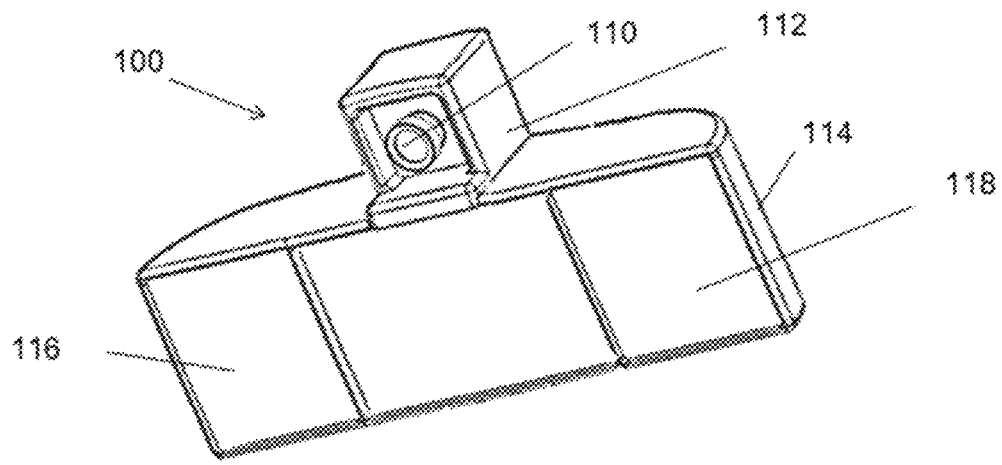
FIG. 6 is a schematic perspective view of the exterior of a camera system in accordance with a second embodiment of the present disclosure.

FIG. 6 is a schematic perspective view of a 3D stereoscopic camera 100 in accordance with a second embodiment of the present invention. The stereoscopic camera 100 in this embodiment is similar to the stereoscopic camera 20 of the previous embodiment in that it comprises a projector 110 which is contained within an upper portion of a housing 112. The projector 110 is similar to the projector 26,27,28 of the previous embodiment. Similarly as with the previous embodiment a lower portion of the housing 114 projects beneath and extends to either side of the upper portion of the housing 112. The lower portion 114 of the housing has a greater depth compared with the housing of the previous embodiment but does not extend as far back behind the upper portion of the housing 112. A first and a second window 116,118 is provided in the front of the lower portion of the housing 114 at either end of the housing remote from the central portion of the housing located beneath the projector 110. Preferably this type of motion monitor camera is especially suitable for setting up in a treatment room, where a collision between different object in the object may occur. This camera is especially suitable for monitoring if a potential collision is to occur, since the construction allow for a very large field of view to be covered.

Figure 7:
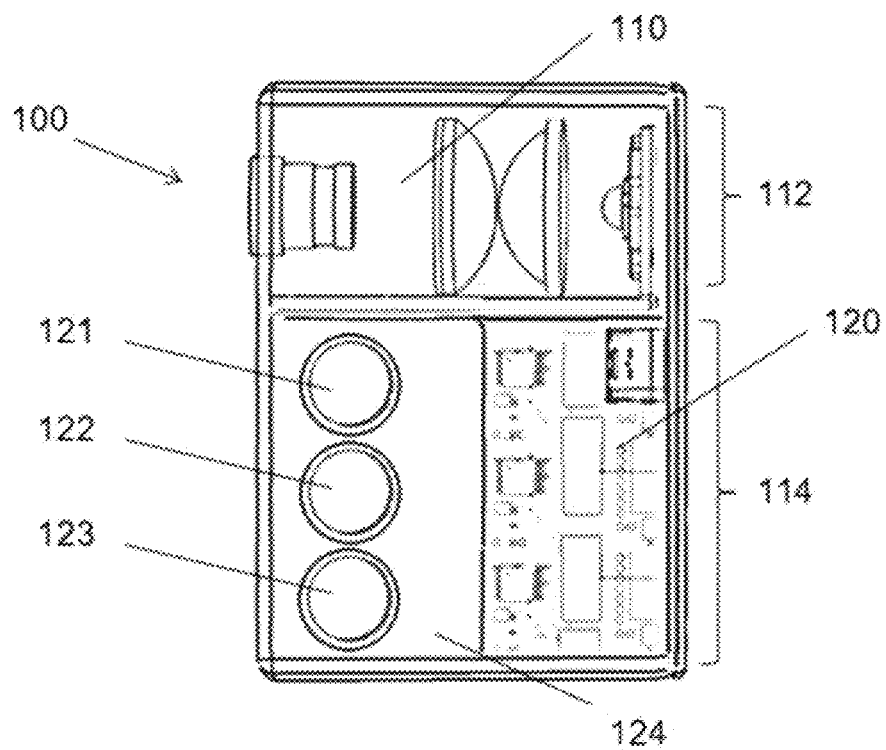
FIG. 7 is a cut away cross sectional view of the camera system of FIG. 6.

As shown in FIG. 7, a circuit board 120 is contained within the lower portion 114 of the housing along with a set of six lens arrangements, three of which 121,122,123 are shown in FIG. 7. In this embodiment as the depth of the lower portion 114 of the housing is greater than in the previous embodiment, the lower portion 114 of the housing is able to contain the entirety of the circuit board 120 without a portion of the circuit board 120 projecting behind the projector 110 and hence the thickness of the camera may be reduced so as not to extend beyond the size necessary to accommodate the projector 110. The lens arrangements 121,122,123 are held in place by a bracket 124. A symmetrical arrangement of three further lens arrangements 125,126, 127 (not visible in FIG. 7) are held in place by another bracket (also not visible in FIG. 7) on the other side of the circuit board 120.

Figure 8:
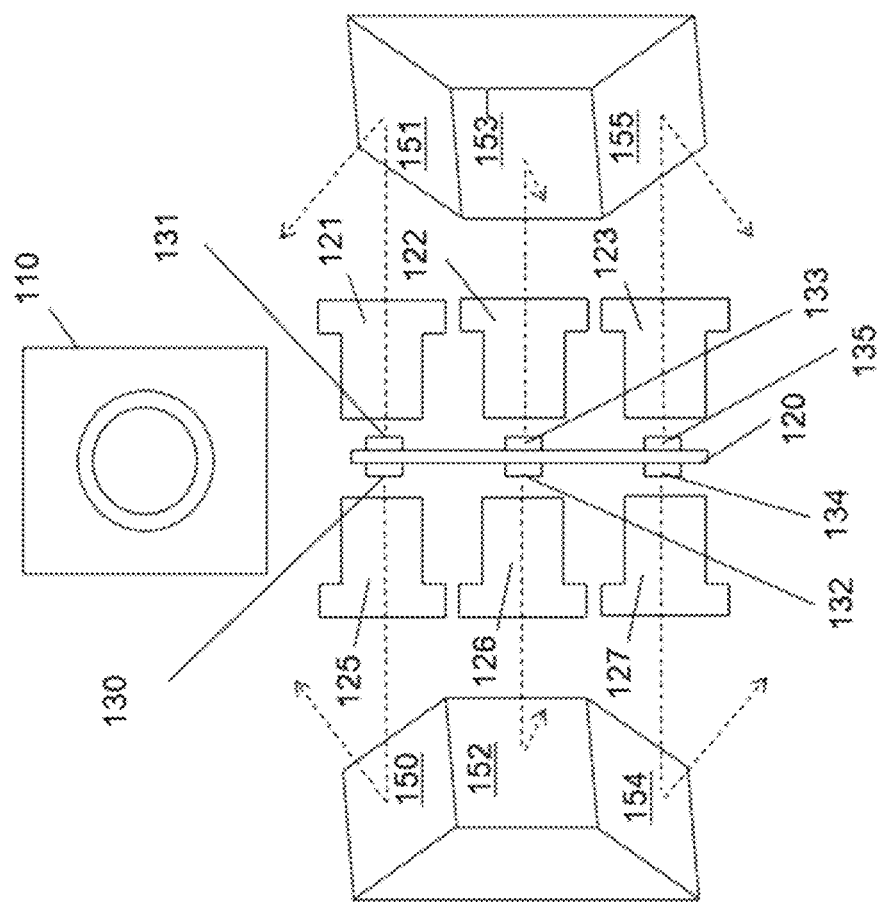
FIG. 8 is a schematic illustration of the arrangement of image sensors and mirrors in the camera system of FIG. 6.

In the previous embodiment, a camera 20 having a first and a second image sensor 36,38 was described. In this embodiment rather than having a single pair of image sensors 36,38, six image sensors 130-135 are provided on the circuit board 120 which together with a specific arrangement of mirrors enables the stereoscopic camera 100 of this embodiment to have a broader angle of view than the camera 20 of the previous embodiment. As is shown in FIG. 8, the image sensors 130-135 are provided on the circuit board 120 as three pairs of image sensors 130 & 131, 132 & 133, 134 & 135 where the image sensors in each pair are provided on opposing sides of the circuit board 120. A lens arrangement 121-123, 125-127 is provided in front of each of the image sensors 130-135. The image sensors 130-135 are arranged to review one of six mirrors 150-155, arranged in two sets of three 150,152,154; 151,153,154 where the mirrors in each set are arranged on the surface of a rhomboid trapezium with the mirrored surfaces angled in at approximately 45° relative to the orientation of the circuit board 120.

In this way the mirrors 152,153 viewed by the central pair of image sensors 132,133 are presented with images via the central lens arrangements 126,122 in a similar way to which the images sensors 36,38 view an object via the lens arrangements 40,44 and mirrors 48,52 in the previous embodiment. The upper pair of images sensors 130,131 are presented with images via an upper pair of lens arrangements 125,121 and the upper mirror surfaces 150,151 of the rhomboid trapezium mirror arrangement and the lower pair of images sensors 134,135 are presented with images via an lower pair of lens arrangements 127,123 and the lower mirror surfaces 154,155 of the mirror arrangement. As the mirror surfaces 150,152,154; 151,153,154 of the mirror arrangements are each angled relative to each other this has the effect of orientating the effective image planes of the upper 130,131 and lower 134,135 image sensors relative to those of the central pair of image sensors 132,133 and thus the combined angle of view of the image sensors 130-135 is greater than the single pair of image sensors 36,38 in the previous embodiment and the camera therefore is able to view a greater portion of a patient than the camera of the previous embodiment.

Although in the above described embodiments specific arrangements of image sensors and mirrors has been described, it will be appreciated that in other embodiments alternative arrangements could potentially be utilized to achieve a reduction in the size of a device. Thus for example rather than obtaining images via a single mirror, images could potentially be obtained via an arrangement of multiple mirrors. Further it will be appreciated that rather than arranging the image sensors, lens assemblies and mirrors symmetrically, an asymmetric arrangement could be utilized.

Although, in the second embodiment, a camera having a single projector 110 has been described, it will be appreciated that in other embodiments additional projectors could be provided if it was desired to increase the volume into which a pattern of light was to be projected where such a volume was viewed by one or more of the image sensors 130-135 via the lens arrangements 121-123,125-127 and the mirrors 150-155.

Although, in the second embodiment, a camera having three pairs of image sensors has been described which enables the camera to have a greater field of view than a camera with a single pair of image sensors, it will be appreciated that the similar advantages could be achieved utilizing two pairs of image sensors or, alternatively, more than three pairs of image sensors.

As will become apparent through out the description of the different embodiments, a plurality of different cameras may be used in the camera monitoring system described herein. One or more of the cameras may be constructed as described in the previous sections, and/or as follows.

Accordingly, it should be noted that throughout the description, a setup camera is defined, which is utilized, at least, to monitor the patient when the patient is being positioned on a couch prior to treatment and/or scanning.

In addition, the camera monitoring system may comprise one or more motion monitor cameras, which are configured to monitor a patient during treatment and/or scanning. This or these motion monitor cameras are throughout the description defined as either "motion monitor cameras" and/or "treatment cameras" and/or as the "centrally positioned camera(s)" The definition centrally positioned should not limit the understanding to a camera being positioned in the middle. Common to all embodiments described herein is that the motion monitor camera is configured to have a field of view oriented towards a target area of a patient during treatment and/or scanning. However, as will be apparent, this or these monitor cameras can be positioned in different configurations in the treatment room/scanning setup.

Figure 9:
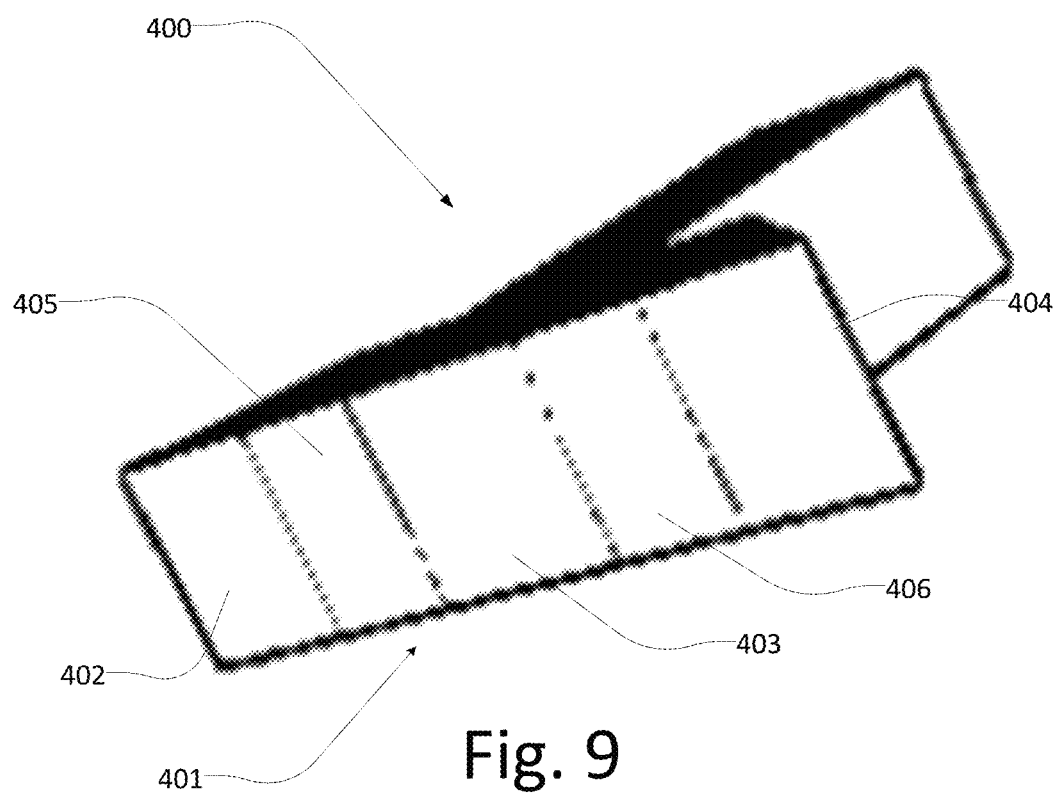
FIG. 9 illustrates an example of a motion and couch monitor camera to be used in the camera monitoring system.
Figure 10:
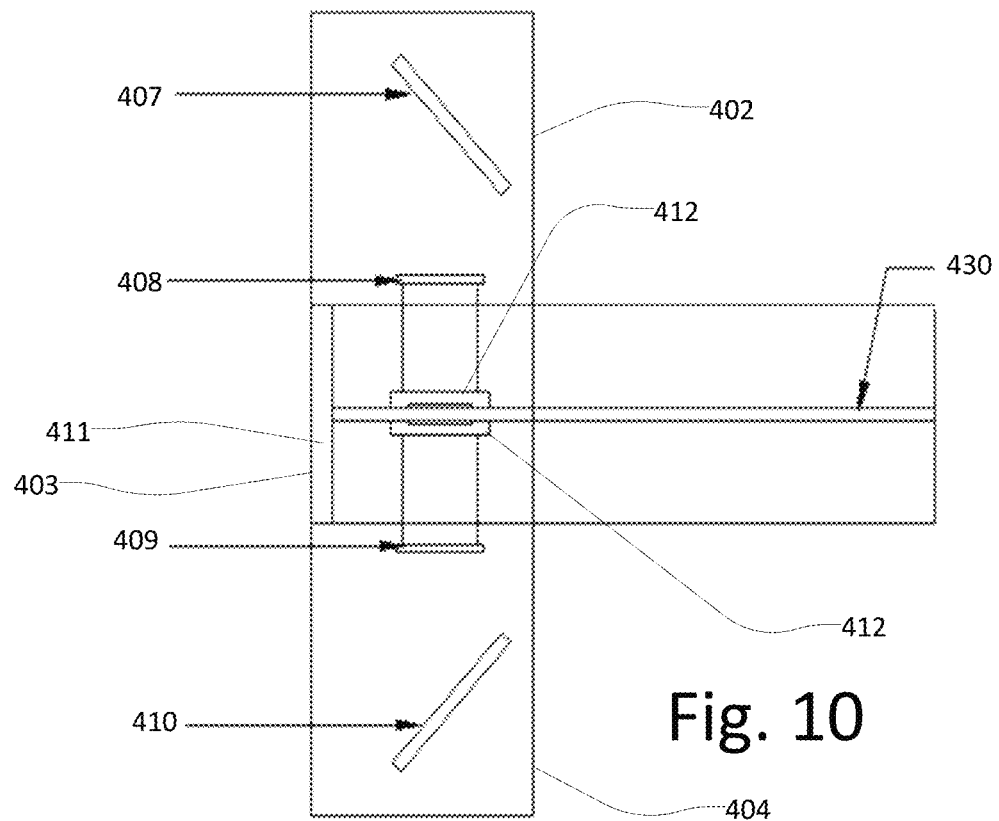
FIG. 10 illustrates internal parts of the motion monitor camera according to FIG. 9.
Figure 11:
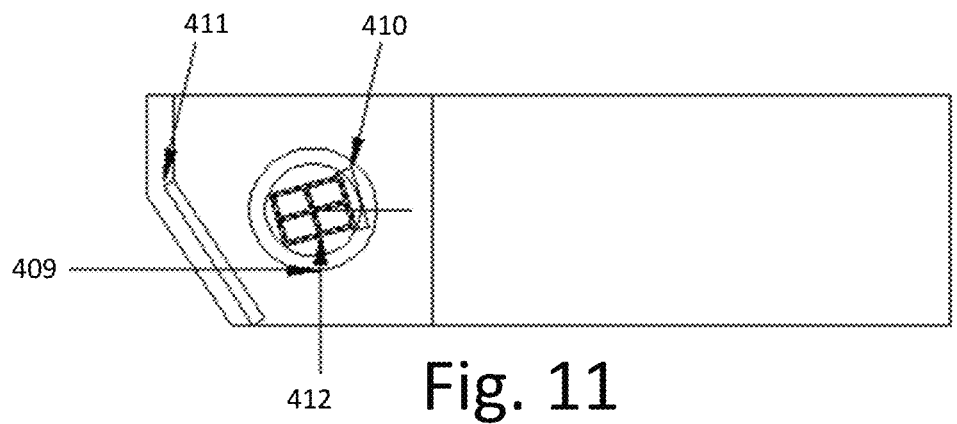
FIG. 11 illustrates a side view of internal parts of the motion monitor camera according to FIGS. 9 and 10.

Turning now to FIGS. 9 to 11 another example than previously described of the motion monitor camera 400 is described. The motion monitor camera 400 comprise a front part 401 configured to be oriented to face at least a surface of a patient and/or calibration object in a medical apparatus. The front 401 comprises substantially five parts, wherein a middle part 403 is configured to contain within the camera 400, a compact projector configured for us in calibration of cameras. The compact projector may be configured as a lens-lens semiconductor solution, such as a vertical cavity surface emitting laser (VCSEL). These type of laser diodes comprises a laser beam emission that are arranged perpendicular from the top surface. Using a VCSEL semiconductor the LED for the purpose of calibration, it is possible to allow for a more compact camera construction, where the projector LED's is configured to reside on the same PCB just a few mm apart unlike a conventional projector that does allow such integration. Thus, it is possible with the camera construction shown in at least FIGS. 9 to 11 to minimize the height of the camera and thus allow for a very compact camera that can be inserted at least into the bore of a bore based medical apparatus.

Furthermore, as illustrated in FIG. 9, the front portion 401 is from the middle configured with a left part 402 and a right part 404, where the left 402 and right 404 parts contains within the camera interior a set of mirrors. The left part 402 and the right part 404 are each distanced from the middle part 403 with the combined projector and calibration unit, by a space within the interior of the camera, which space is covering by two front covers 405, 406. In general, the construction of the camera as described herein allows for an easy re-construction of the camera, due to the fact that the only the mirrors needs to be distanced from each other to provide another working distance of the camera. Thus, the circuit board and lenses with the positioning and construction in the middle of the camera, allows for these featuring remaining in place, while only a movement of the mirrors are needed, if a change in working distance is preferred.

Turning now to FIG. 10, the internal parts of the motion monitor camera in FIG. 9 is illustrated in more detail. As seen, and in correspondence with the embodiments of FIGS. 3 to 5 and FIGS. 6 to 8, the camera generally comprises in the left part 402 a first mirror 407 and correspondingly in the right part 404 a second mirror 410. The middle part comprises a first lens 408 and a second lens 409, which first and second lenses 408, 409 are positioned on each side of a PCB 430. The PCB 430 is configured to be arranged as described in relation to FIGS. 5 and 8. However, in the embodiment illustrated in FIG. 10 a further projector PCB 411 is illustrated. This projector PCB 411 is connected to the PCB 430, wherein the projector PCB comprises a projector which is configured to create a low power interference pattern. As is seen in the Figure the projector PCB 411 is oriented substantially perpendicular to the plane of the camera PCB 430. The projector of the projector PCB 411 is configured to substantially orient the interference pattern towards an object, such as a surface of a patient, being imaged. Thus, as illustrated, the projector is substantially integrated into the lower portion 24 as previously defined in relation to embodiments described herein. Thus, in the embodiment illustrated in FIGS. 9 to 11 does not contain a top portion as in other embodiments described herein. This enables a substantially smaller camera.

When turning to FIG. 11, a side view of the motion monitor camera of FIGS. 9 and 10 is illustrated. As illustrated in FIG. 11 and previously described, this type of motion monitor camera is constructed with an integrated projector having a projector PCB 411. Furthermore, this motion monitor camera is optimized for use in a bore based medical apparatus due to the internal construction and orientation of the mirrors and the image sensors in relation to each other. That is, when the monitor camera is mounted within a bore based system, as explained in embodiments described herein, the mirrors inside the camera is configured to point inwards and downwards in relation to the surface of the bore in which the cameras are mounted. Thus mirrors 407, 410 is as illustrated in FIG. 10 angled to point towards the center of the camera, defined e.g. by a plane of the camera PCB 430. At the same time, as more accurately illustrated in FIG. 11, the mirror 410 (and mirror 407, not shown) is pointing in a direction downwards in relation to the surface of the bore based apparatus to which the cameras is mounted or at least abutting. Such mirror orientation will in the images obtained by the cameras cause the images to appear rotated. Such rotation of the images recorded by these type of monitor cameras is however avoided by the cameras being configured with a substantially rotated sensor. This is in more detail illustrated in FIG. 11, wherein it can be seen that the mirror 410 and the sensor 412 is angled in such way that the mirror 410 and sensor 412 comprises a substantially perpendicular view plane. In other words, the 3D camera is configured to be inserted in a bore of the bore based medical apparatus along an inside top surface of the bore in such manner that a top portion of the camera is substantially aligned with the inside top surface of the bore, wherein the camera is configured with the first mirror and the second mirror being angled in a direction downwards from the top portion of the camera towards the bottom portion of the camera, and wherein further the first and second mirror is angled inwards toward the center of the camera, wherein further, the first and second sensor are arranged in relation to the first and second mirror, so as to provide a substantially perpendicular view plane from the first and second mirror.

In view of the embodiments described herein, other types of cameras may also be used in the camera monitoring system. That is, in embodiments described herein also one or more setup cameras are used to monitor the positioning of a patient during a setup stage. These setup camera types of cameras may be different from the motion monitor cameras, in that they may be configured with a different working distance defined as the distance between the patient and the camera. Alternatively, the same types of camera construction can be used for both the setup cameras and the monitor cameras. In other words, As will become apparent, a third type of camera may form part of the camera monitor system. This third type of camera, i.e. a couch monitor camera, may be constructed slightly different from the first type setup camera and the second type motion monitor cameras. That is, the third type of camera is primarily configured and arranged in the treatment/scanning setup to have a field of view covering the couch or a uniquely identifiable feature mounted on the couch. Furthermore, the couch monitor camera may be configured with an illumination object configured to illuminate objects arranged within the field of view of the couch monitor camera.

Figure 21:
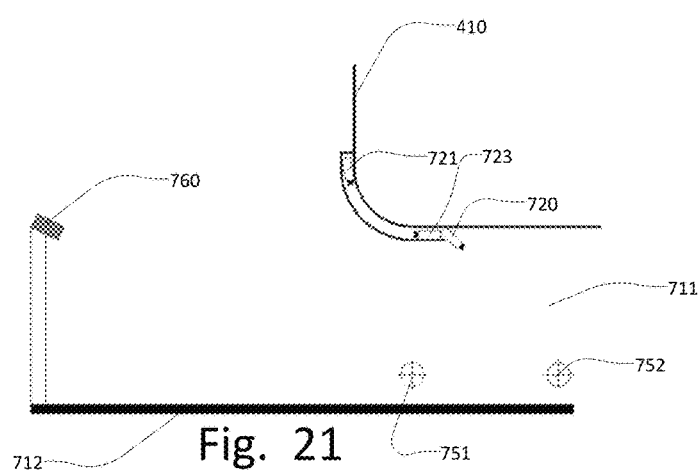
FIG. 21 illustrates a sideview of a camera monitoring system in a setup in relation to a bore based medical apparatus.
Figure 21A:
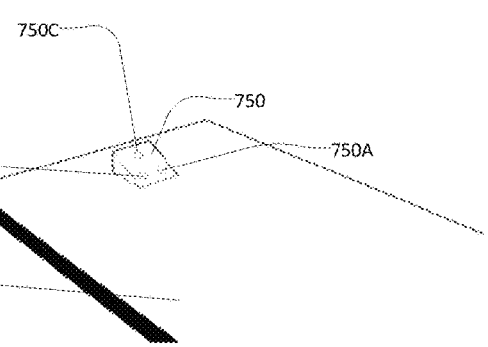
FIG. 21A illustrate a couch of a bore based medical apparatus having a couch maker.

Especially, the couch monitor camera may in an embodiment, be a stereo vision camera optionally comprising a near infrared LED to illuminate retroreflective markers on the couch, as described in relation to FIG. 21A.

Alternatively, the markers arranged on the couch could be active markers, in which embodiment, no illumination from the couch monitor camera would be required, since the markers would lit up themselves.

In an alternative embodiment, the couch may be configured with a structure and/or object with uniquely defined features provided thereon, wherein a tracking of the features via the couch monitoring camera may be used to track couch movement, as described in relation to FIG. 21. The couch position may also be determined by recalling couch locations determined during couch calibration or via feedback mechanism in the couch control system. Accordingly, in an embodiment, a set of stored offset values related to any potential couch movement offset, between the setup camera position and the treatment position could be utilized in a calibration setup to account for any sag/drift that the couch is known to be prone to experience during movement of the couch. Another option could be to utilize a feedback signal provided by the couch to adjust for any offset by the couch.

Further details and use of the couch monitoring camera will become apparent in the description of FIGS. 19 to 22.

Figure 12:
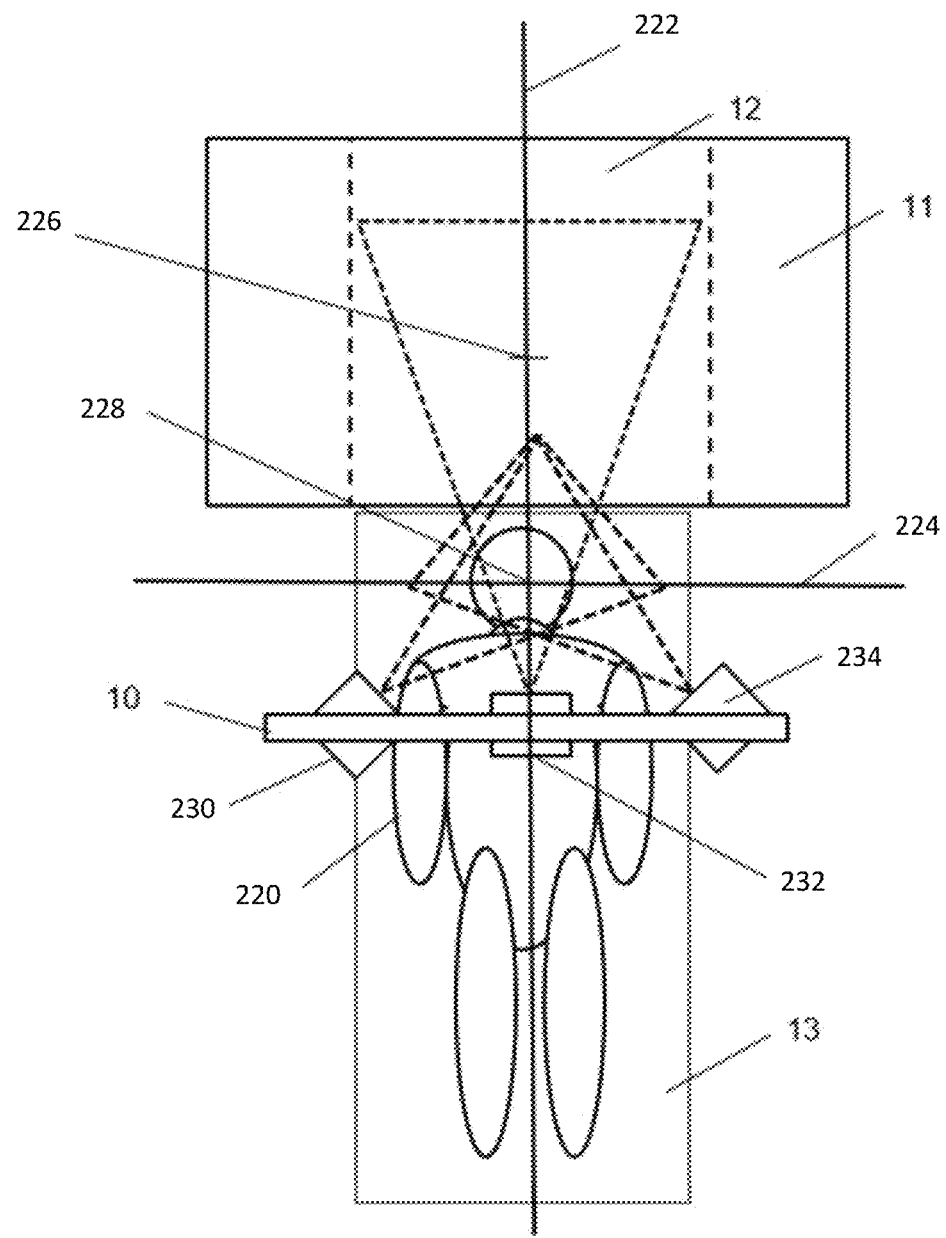
FIG. 12 is a schematic plan view of a patient on a mechanical couch in a set up position.
Figure 13:
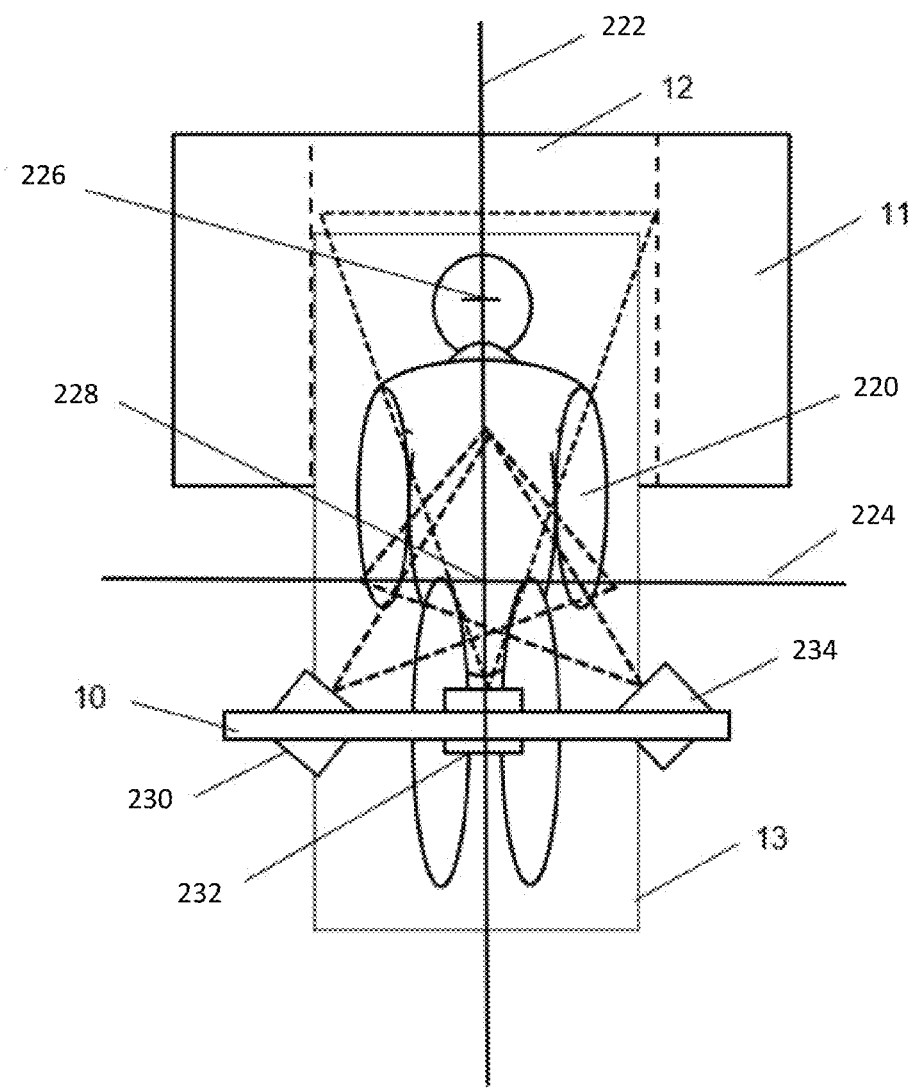
FIG. 13 is a schematic plan view of the patient on a mechanical couch of FIG. 12 in a treatment position.

Turning now to FIGS. 12 to 16, an exemplified embodiment of calibration a camera monitoring system as described herein is now described. Referring initially to FIG. 12, a schematic plan view of a patient 220 on the mechanical couch 13 in a set up position located in front of the bore 12 of the treatment apparatus 11 is illustrated. FIG. 13 is a schematic plan view of the patient 220 on the mechanical couch 13 of FIG. 12 in a treatment position.

In the embodiments illustrated in the Figures, a laser lighting system (not shown) projects a first plane of laser light 222, a second plane of laser light 224 and a third plane of laser light (third plane of light not shown) to facilitate the positioning of the patient 220. The first plane of light 222 is aligned with the treatment room iso-center 226 (i.e. the point in space where the treatment apparatus 11 is arranged to direct a radiation beam) along an axis, along which the mechanical couch 13 is arranged to enter into the bore 12 of the treatment apparatus 11. The second plane of light 224 is arranged perpendicular to the first plane of light 222 and to intersect the first plane of light 222 at a point 228 a fixed distance in front of the treatment room iso-center 226. The third plane of light (not shown) is projected so as to be mutually perpendicular to the first and second planes of laser light at a level corresponding to the height of the treatment room iso-center 226.

The patient monitoring system 10 in this example comprises three cameras 230, 232, 234. The cameras 230, 232, 234 are arranged so that a centrally positioned camera 232 looks into the bore 12 of the treatment apparatus 11, whereas two outer cameras 230, 234 are arranged to view a set up area in the front of the treatment apparatus 11. The setup area is centered substantially on the point 228 highlighted by the intersection of the planes of laser light 222, 224. The outlines of the fields of view of the cameras are shown in FIGS. 12 and 13 by dashed lines emanating from the cameras 230, 232, 234. In other words, the two cameras 234, 230 constitutes a set of setup cameras 230, 234, which are configured to record images of the patient 220 during positioning of the patient 220 onto the couch 13.

In use, initially a patient 220 is positioned on the mechanical couch 13 with the mechanical couch 13 in the setup position shown in FIG. 12. In this setup position, the patient 220 is positioned so that the portion of the patient 20 which is to be irradiated (also denoted the target area of the patient) is located at the point 228 highlighted by the laser lighting system. In the setup position, the surface of the patient 220 is viewed by the two outer cameras 230, 234 (i.e. the two setup cameras) of the patient monitoring system 10, whereby the patient monitoring system (also denoted camera monitoring system or merely monitoring system throughout the disclosure), via a processor enables a model surface of the patient 220 to be generated and compared with a previously stored model so that any differences between the generated surface and the stored model surface can be identified and the positioning of the patient 220 adjusted so that the surface of the patient 220 matches the surface defined by the stored model. In other words, the setup cameras 230, 234 records images of the patient 220 lying on the couch and transmit these images to a patient monitor processor. The processor is configured to generate a computer surface model of the patient, which computer surface model is compared to a previously computer model of the same patient. If any deviation between the stored model and the generated model is present, a clinician is notified and the patient, as the patient is currently lying on the couch, should be repositioned, such that the actual couch position of the patient, and the subsequent update of the generated computer surface model corresponds with the stored computer model.

Subsequently, during treatment the mechanical couch 13 is translated by a fixed amount so as to be moved into the position illustrated in FIG. 13. In this position the portion (i.e. the target area) of the surface of the patient 220 which was previously viewed by the two outer cameras 230, 234 (i.e. also denoted the setup camera(s) throughout the description) of the patient monitoring system 10 is now viewed by the central camera 232 (also denoted as a motion monitor camera throughout the description) of the patient monitoring system 10 which again enables a model of the surface of the patient 220 to be generated and compared with a stored model so as to detect any deviation of the positioning of the patient 220 from an expected position.

Thus, in other words, the monitoring system, which is also throughout the description defined as a camera monitoring system or a patient monitoring system, comprises at least one motion monitor camera configured to record images of at least a target area of the patient lying on the couch during use of the medical apparatus, such as a radiotherapy system, CT scanner, MR scanner or a combination thereof. Furthermore, the monitoring system comprises at least one setup camera, which is configured to record images of at least the same target area during a positioning of the patient onto the couch prior to treatment or scanning.

In theory, as the mechanical couch 13 is translated by a fixed amount corresponding to the fixed distance between the point in space highlighted by the laser lighting system 228 and the treatment room iso-center 226, the repositioning of the couch 13 should cause the portion of the patient previously located at the point in space 228 highlighted by the laser lighting system to be located at the treatment room iso-center 226, where the target area of the patient will be irradiated by the treatment apparatus 11. In practice, however, mechanical couches are subject to a certain amount of sag and other mechanical inaccuracy. For this reason, the accuracy of the positioning of the mechanical couch 13 needs to be checked frequently. However, even if this is the case, there is a possibility that a patient 220 will not be correctly positioned when errors arise between these checks.

The illustrated patient monitoring system 10 provides a means for detecting potential deviations arising due to physical and mechanical errors in positioning by the mechanical couch 13. In order to do so, it is necessary that the models of a surface of a patient 220 generated when the patient 220 is in the setup position and the treatment position are consistent. In particularly, the models generated based on images from the outer cameras 230, 234 need to be consistent with the models generated based on images from the central camera 232. This consistency can be achieved by calibrating the patient monitoring system, so that models generated based on images of a patient located in the set up location and the treatment location are generated in two model spaces which are offset relative to one another by a translation corresponding to the difference between those two locations.

A method of calibrating the monitoring system 10 which achieves this consistency will now be described with reference to FIGS. 14 to 16.

Figure 14:
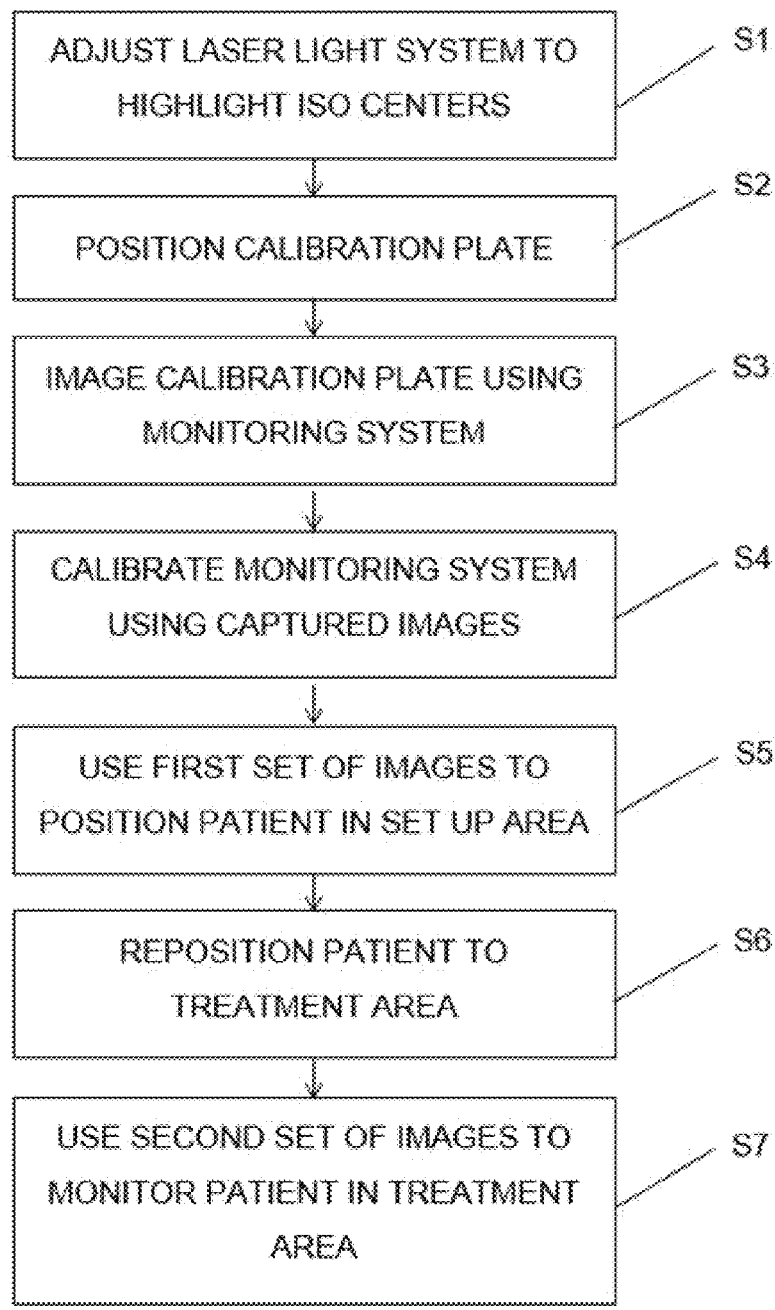
FIG. 14 is a flow diagram of the use of a monitoring system calibrated in accordance with an embodiment of the present disclosure.

Turning first to FIG. 14 which is a flow diagram of the use of a monitoring system 10 calibrated in accordance with an embodiment of the present disclosure. In an initial step (S1) a laser lighting system is set up so as to identify the locations of the treatment room iso-center 226 and a fixed position 228 located a set distance away from the treatment room iso-center 226.

Typically, this will be achieved in a two-step process. Initially the identification of the location of the treatment room iso-center 226 can be established using conventional techniques such as were described in the introduction of this patent and then the laser lighting system is set up to project a plane of light 222 passing through the treatment room iso-centre 226. Preferably, this plane of light 222 is aligned with the axis along which the treatment room couch 13 is arranged to move. A second plane of laser light 224 can then be set up to be projected a fixed distance from the identified portion of the treatment room iso-center 226 and the third plane of light (not shown) is set so as to mutually perpendicular to the first and second planes Having adjusted the laser lighting system so that the laser lighting system projects planes of light 222, 224 passing through the selected fixed point 228 a distance from the treatment room iso-center 26, where one of the planes of light 222 also passes through the treatment room iso-center 226 itself, a calibration object, which in this embodiment is in the form of a calibration plate, is placed on the mechanical couch 13 and aligned (S2) with the planes of laser light 222, 224 projected by the laser lighting system.

Figure 15:
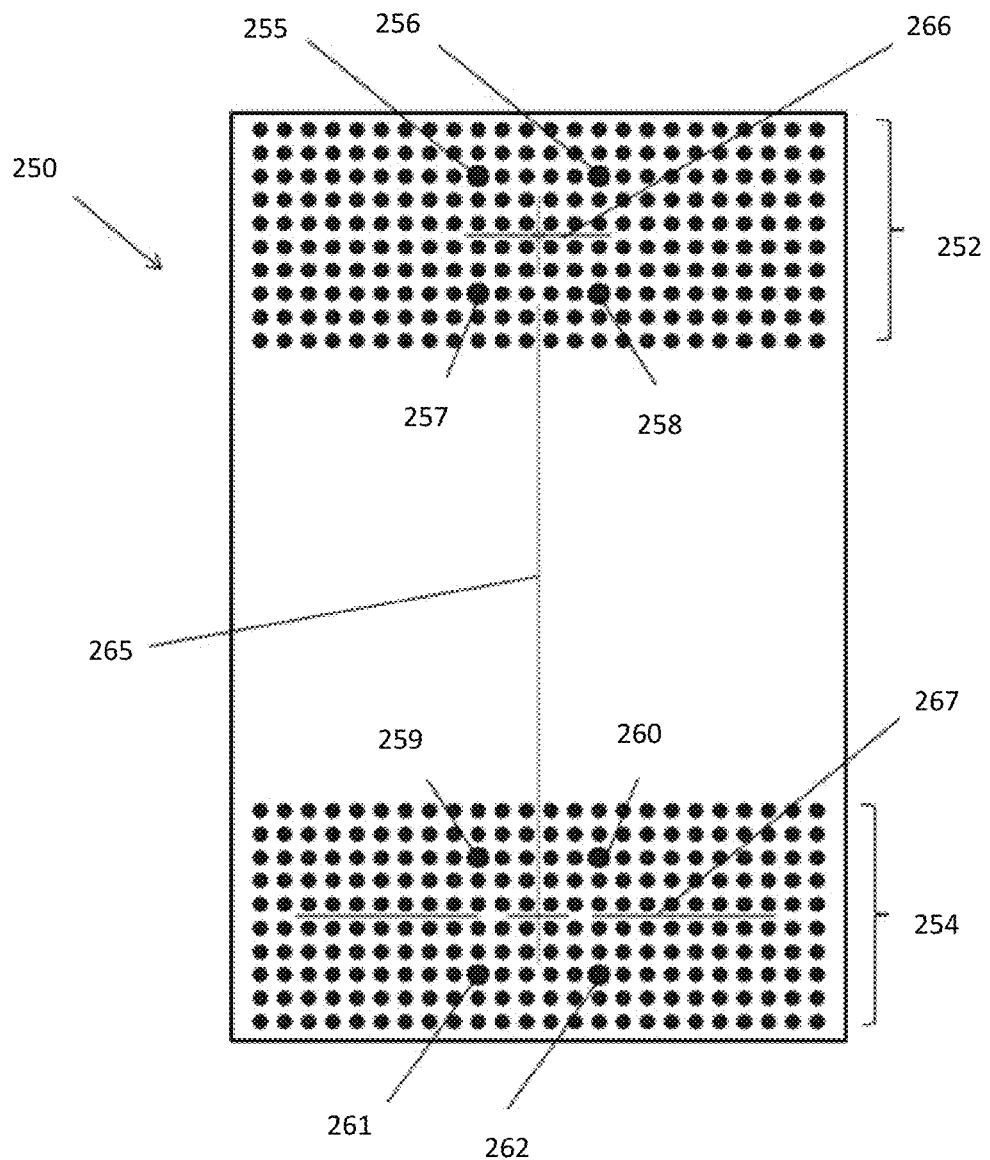
FIG. 15 is a plan view of an exemplary calibration plate for use in an embodiment of the present disclosure.

FIG. 15 is a plan view of an exemplary calibration plate 250 for use in embodiments of the monitoring system as described herein.

In an embodiment, the calibration object 250 is in the form of a rectangular calibration plate 250 which is made of a stiff rigid material such as aluminum onto which a high precision pattern of calibration markings have been machined or printed. In this embodiment the calibration markings comprise two sets of calibration markings 252, 254, one set in either end of the calibration plate 250, each set of calibration markings 252, 54 comprising an array of circles. As illustrated in FIG. 15 the two set of calibration markings is configured to cover opposite end areas of the calibration plate 250 and is configured with a center area of each of the calibration marking areas. In each of the center areas, four circles 255-262 are defined, wherein the four circles are configured with a slightly greater radius than the other circles of the calibration marking areas. The centers of the larger circles 255-258, 259-262 in each of the sets of calibration markings 252, 254 correspond to the corners of a square.

Additionally, the calibration markings also comprise a set of lines 265-267 etched on the surface of the calibration plate 250, the lines comprising a center line 265 extending along the center of the calibration plate and two cross lines 266, 267 perpendicular to the center line 265. The two cross lines 266, 267 intersect with the center line 265 at positions corresponding to the centers of the squares, the corners of which correspond to the centers of the larger circles 255-258, 259, 262 in the calibration markings. The distance between the points of intersection between the center line 265 and the two cross lines 266, 267, correspond to the offset between the treatment room iso-center 226 and the point of intersection 228 of the planes of light 222, 224 projected by the laser light projection system.

Figure 16:
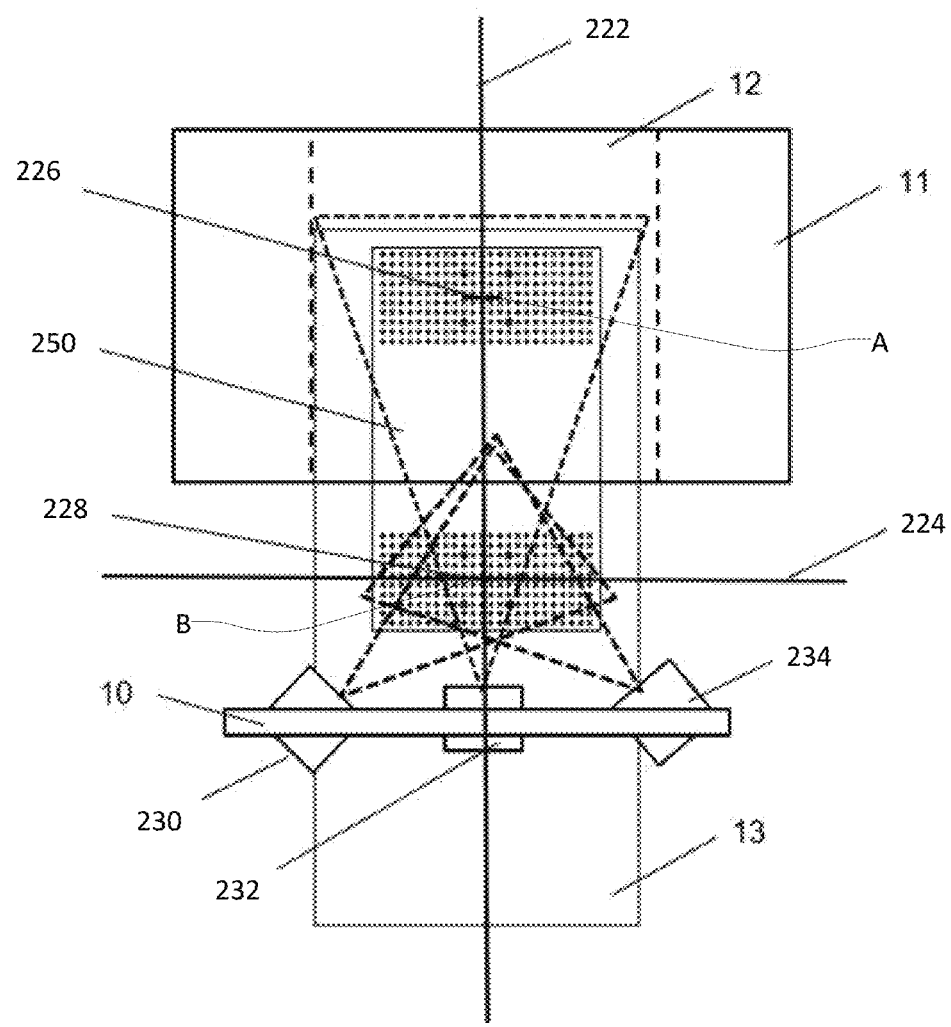
FIG. 16 is a schematic plan view of the exemplary calibration plate of FIG. 15 positioned on the mechanical couch of FIGS. 12 and 13.

FIG. 16 is a schematic plan view of the exemplary calibration plate 250 positioned on a mechanical couch 13 of the treatment system of FIGS. 12 and 13. FIG. 16 thus, illustrates the couch 13 in a treatment position with the planes of laser light 222, 224 from the laser highlighting system aligned with the center line 265 and one of the cross lines 267 of the calibration plate 250. Due to the correspondence of the distance between the points of intersection of the cross lines 266, 267 with the center line 265, with the distance between the point 228 highlighted by the intersection of the planes of laser light 222, 224 and the treatment room iso-center 226, aligning the cross line 267 and the center line 265 with the planes of laser light 222, 224 with the calibration plate 250 flat and the laser light of the third plane of laser light skimming, the surface of the calibration plate 250 causes the point of intersection between the other cross line 266 and the center line 265 to be positioned at the treatment room iso-center 226.

With the calibration plate 250 placed in this position (i.e. the treatment position as illustrated in FIG. 16), images of the two calibration sets of calibration markings 252, 254 can be captured (S3) by the cameras 230-234 of the monitoring system 10. More specifically, images of the set of calibration markings 252 located in the vicinity of the treatment room iso-center 226 are captured by the center camera 232 of the monitoring system 10 and images of the set of calibration markings 254 in located in the vicinity of the point of intersection 228 of the planes of laser lighting 222, 224 are captured by the two other cameras 230, 234 of the monitoring system 10.

The images obtained by the cameras 230-234 can then be used (S4) to calibrate the monitoring system 10.

To achieve this, initially the images captured by the cameras 230-234 are processed to identify within the images the positions of the larger circles 255-258, 259-262 on the calibration plate 250 as they appear in the images. This can be done either automatically using conventional techniques or alternatively, a user may identify the four circles manually.

From the relative positions of circles 255-258; 259-262, for each image a first projective transformation is determined which accounts for the estimated centers of the identified circles, wherein the estimated centers define the corners of a projected distorted square due to the relative orientation of the calibration plate 250 and the camera 230; 232; 234 obtaining the image.

This calculated transform is then utilized to determine estimated three-dimensional co-ordinates centers of each of the circles in the calibration area 252; 254 imaged by the camera 230; 232; 234. These calculated co-ordinates centers are then used to identify an estimated location and orientation for a plane corresponding to a surface of the calibration plate 250 relative to the position, from which an image has been obtained.

Each pixel in the image obtained by each camera 230; 232; 234 is then processed in turn to determine where, within the plane containing the estimated positions of the circle centers, each pixel corresponds. The estimated circle centers are then processed in turn and the pixels in an image corresponding to points lying within a pre-determined distance from each circle center in the calculated plane are then identified. These areas can be selected to encompass points lying within the plane of the calibration plate 250 up to a distance slightly larger than the radius of the circles appearing on the calibration plate 250. Thus, in this way for each circle a set of pixels is identified which correspond to the appearance of a portion of the plate centered on the estimated center position and extending slightly beyond the outer edge of the circle in question. The grey scale values for each of the pixels in each set are then utilized to determine an improved estimate of the co-ordinates for the circle centers. x and y co-ordinates for the positions of the points in the estimated plane including the surface of the calibration plate each pixel represents within the set is determined. These calculated x and y co-ordinates are then utilized to estimate an improved estimate of the x,y co-ordinates of the circle center.

Co-ordinates for the points within the image corresponding to the new estimated circle centers are then determined from these x,y co-ordinates and these updated estimates of the centers of the larger circles 255-258; 259-262 are then utilized to determine a more accurate estimated transformation to account for the location and orientation of the calibration plate 250. The above process can then be repeated until an accurate estimate of the actual circle center positions is made and the true (i.e. a final) transform required to account for the relative orientation of the calibration plate 250 is determined.

Using the final determined transform, the expected positions of all of the circles on the calibration plate 250 appearing in the images captured by the cameras 230-234 are then calculated. For each of the circles a set of pixels is identified corresponding to points within a preset distance to the circle center and then an improved circle centre co-ordinate is calculated using the grey scale values for these portions of the images.

When the co-ordinates for all the centers of each of the representations of the circles on the calibration plate 250 as viewed by a camera 230; 232; 234 have been calculated, the relative orientation of the central camera 232 to the treatment room iso-center 226 and the other cameras 230, 234 to the point in space highlighted by the intersection 228 of the planes of laser light 222, 224 can then be calculated from the relative positions of these points in the images and the known relative locations of these circles on the surface of the calibration sheet as is described in detail in "A Versatile Camera Calibration Technique for High Accuracy 3D Machine Vision Metrology Using Off the Shelf TV Cameras and Lenses, Roger Tsai, IEEE Journal of Robotics and Automation, Vol. Ra-3, No. 4, August 1987 which is hereby incorporated by reference. Further, from the relative positions of the points in the individual images corresponding to the markings on the calibration plate 250, internal camera parameters such as the focal length and radial distortion within the camera images can also be determined.

By calibrating the monitoring system on the basis of the two sets of calibration markings 252, 254 on the calibration plate 250, which are separated by a fixed distance corresponding to the distance between the treatment room iso-center 226 and the position 228 highlighted by the intersection of the planes of laser light 222, 224, the model spaces for models generated by the central camera 232 and the outer two cameras 230, 234 are arranged to be offset by a translation corresponding to the physical distance between those two points 226, 228.

Subsequently, in use, when a patient 220 is positioned on the mechanical couch 13 with the mechanical couch 13 in a set up position such as is illustrated in FIG. 12, a model of a portion of a patient 20 can be generated (S5) on the basis of images obtained by the outer two cameras 230, 234 of the monitoring system 10 using the calibration data identifying the relative location of the cameras 230, 34 relative to the point in space highlighted by the intersection 228 of the planes of laser light 222, 224.

When the patient is then repositioned (Ss6) into a treatment position such as is illustrated in FIG. 13, this portion of the patient 220 will be imaged by the central camera 232 of the monitoring system 10 enabling a model of the imaged portion of the patient 220 to be generated (s7). In the case of a model generated using images obtained by the central camera 232 such models will be generated utilizing the calibration data identifying the relative location of the central camera 232 relative to the treatment room iso-center 226 rather than the relative location of the central camera 232 to the point in space highlighted by the intersection 228 of the planes of laser light 222, 224.

Theoretically, if the physical translation of the mechanical couch 13 accurately corresponds to the offset between the highlighted set up location 228 and the treatment room iso-center 226, the models generated by processing images from the outer two cameras 230, 234 and the central camera 232 should correspond. Where any differences arise, this should identify positioning errors either of the mechanical couch 13 or if the patient 220 has moved whilst being relocated from the set up location to the treatment location.

In this way, the calibration of the monitoring system 10 enables the monitoring system 10 to identify errors in patient positioning which may arise due to inaccuracies in movement of the mechanical couch 13 or patient movement. Furthermore, the detection of such errors is achieved without the monitoring system 10 having to keep the patient under observation throughout the movement of the patient 220 between the set up position and a treatment position.

The above approach simplifies the processing of image data to enable models in different positions to be compared. When processing images from the cameras 230, 232, 234 of the monitoring system 10, no allowance needs to be made for the fact that a patient 220 is located in a different location when generating models from the images of either the outer two cameras 230; 234 or alternatively the central camera 232. The co-ordinates of models in the model spaces generated by the outer two cameras 230; 234 and the central camera 232 automatically account for the distance between the treatment room iso-center 226 and the point in space 228 highlighted by the laser lighting system.

A further example of the use of the calibration method in accordance with the present invention will now be described.

In addition to being suitable for calibrating a monitoring system 10 for monitoring for the movement of a patient 220 between a set up position and a treatment position, the above method may be adapted for monitoring for patient movement in other situations where a patient is translated between multiple treatment locations.

Figure 17:
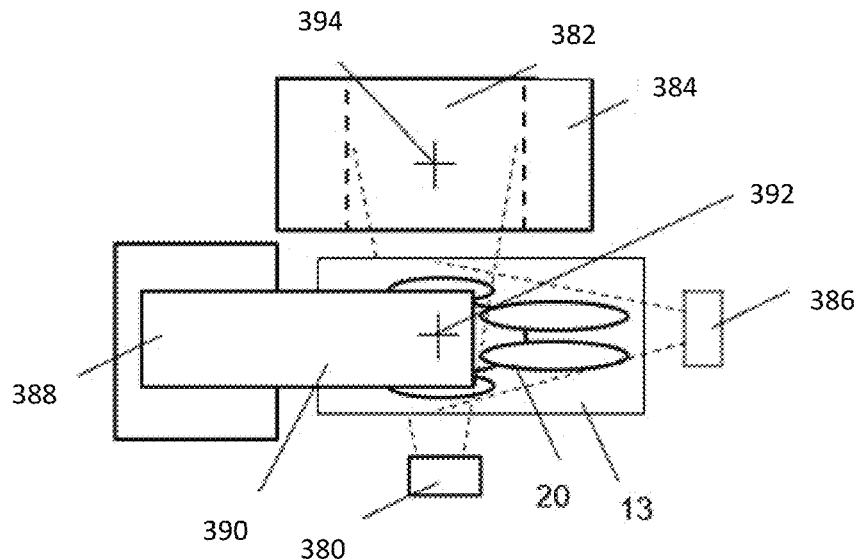
FIG. 17 is a schematic plan view of the patient on a mechanical couch of a combined radiation therapy treatment and imaging apparatus.
Figure 18:
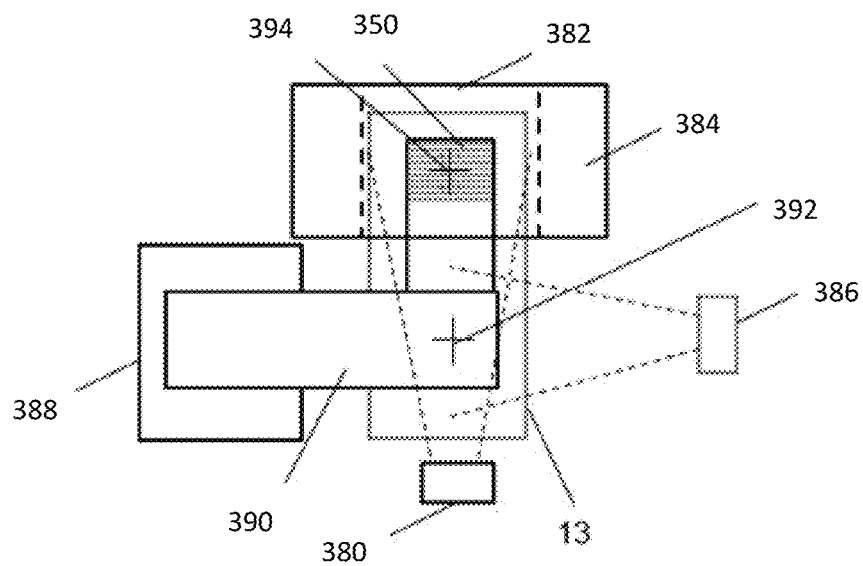
FIG. 18 is a schematic plan view of a calibration plate positioned on a mechanical couch of the combined radiation therapy treatment and imaging apparatus of FIG. 17.

FIGS. 17 and 18 are schematic plan views of a combined radiation therapy treatment and imaging apparatus. In FIG. 17, the combined radiation therapy treatment and imaging apparatus is shown in use with a patient 220 on a mechanical couch 13 in a treatment position whereas in FIG. 18 the mechanical couch 13 is shown in an alternative orientation supporting a calibration plate 350 for calibrating a patient monitoring system.

In this example a first monitoring system 380 is arranged to monitor a patient 220 when the patient 220 is located within a bore 382 of an imaging apparatus 384, for example a CT or MRI scanner or the like. Whereas a second monitoring system 386 is arranged to monitor a patient 220 when the patient 220 is to be irradiated by a radiation therapy machine 388. In this example the radiation therapy machine 388 comprises a gantry 390 which is arranged to rotate about a treatment room iso-center 392 facilitating, together with the movement of mechanical couch 13 (which in this example is a mechanical couch on a robotic arm), the irradiation of a patient 220 from multiple different angles and orientations.

In use when the mechanical couch 13 is orientated in a treatment position (illustrated in FIG. 17) radiation is directed towards the treatment room iso-center 392 which is located at a position corresponding to a target area of the patient. In other words, the target area of the patient which is to be treated with radiation therapy is configured to be positioned at the iso-center of the treatment room, to ensure that only the target area is exposed to radiation. In order to obtain images of the internal anatomy of the patient 220 to identify the target area, periodically, the mechanical couch 13 is rotated and translated so as to locate this portion of a patient to a fixed position 394 in the center of the bore 382 of the imaging apparatus 384. In the illustrated example this second fixed position 394 is displaced from the treatment room iso-center 392 along a plane which is at right angles to the axis about which the gantry 390 of the radiation therapy machine 388 is arranged to rotate.

When calibrating the monitoring apparatus 380, 386 for monitoring the positioning of a patient 220, the mechanical couch 13 can be positioned as shown in FIG. 18 and a calibration plate 350 can be placed on the mechanical couch 13 such that the centers of areas of the calibration plate 350 bearing calibration markings are located at the treatment room iso-center 392 and the center 394 of the bore 382 of the imaging apparatus 384 respectively. This can be achieved by calibration markings being separated from one another by the known fixed distance between the treatment room iso-center 392 and the center 394 of the bore 382 of the imaging apparatus 384 and aligning the calibration plate 350 based on the projection of laser lights from a laser lighting system (not shown) highlighting the treatment room iso-center 392 and the center 394 of the bore 382 of the imaging apparatus 384.

Images of the patterns of calibration markings can then be obtained by the first monitoring system 380 and the second monitoring system 386 and the relative positions of the image planes of cameras of the first and second monitoring systems 380, 386 relative to the center 394 of the bore 382 of the imaging apparatus 384 and the treatment room iso-center 392 can then be determined on the basis of images of the calibration markings as captured by the monitoring systems 380, 386.

In the case of a calibration plate 350 bearing markings similar to those illustrated in FIG. 15, in which the location and orientation of cameras of a monitoring system are determined bases on identification of a set of circles 255-258; 259-262 corresponding to the corners of a square, the calibration of the system can be such so as to take account of the rotation of a patient 220 by 90° between an imaging position and a treatment position as will now be explained.

When positioned as shown in FIG. 18, images of the first set of calibration markings 252 are obtained by the first monitoring system 380 and images of the second set of calibration markings 254 are by obtained the second monitoring system 386. The images of the first set of calibration markings 252 obtained by the first monitoring system 380 are then processed based on the identification of specific circles 255-258 in the first set of calibration markings 252 as being the corners of a square, for example identifying circle 255 as the top left hand corner of the square, circle 256 the top right hand corner of the square, circle 257 the bottom left corner of the square and circle 258 the bottom right hand corner of a square. Images of second set of calibration markings 254 obtained by the second monitoring system 386 are then processed based on the identification of the specific circles 259-262 in the second set of calibration markings 254 defining the corners of a square, for example identifying circle 261 as the top left hand corner of the square, circle 259 the top right hand corner of the square, circle 262 the bottom left corner of the square and circle 260 the bottom right hand corner of a square. By identifying the specific circles from the first set of calibration markings 252 and second set of calibration marking 254 as corners of squares which are rotated relative to each other by 90° this causes the first and second monitoring systems 380, 386 to be calibrated so that the model spaces of the first and second monitoring systems 380, 386 are rotated by 90° as well as being translated by the distance corresponding to the distance between the treatment room iso-center 392 and the center 394 of the bore 382 of the imaging apparatus 384 and hence facilitate a comparison between the models generated by the two monitoring systems.

Although in the above two specific examples of monitoring systems and calibration methods have been described, it will be appreciated that various details of the monitoring systems and calibration method could be varied.

Thus, for example in the second described example, an imaging apparatus 384 and treatment apparatus 388 have been described as being at right angles to one another and the system has been described as accounting for the rotation of a patient between an imaging position and a treatment position by identification of specific circles with the corners of a square. It will be appreciated that in other embodiments, other angles of rotation could be accounted for by providing patterns of calibration markings on a calibration plate 250 where some of the markings are rotated by a predetermined angle so that markings in two different areas, the areas to be located in the vicinity of the treatment room iso-center and an imaging iso-center, are angled at an angle corresponding to the fixed angle of rotation between a treatment position and an imaging position and hence when calibrated the monitoring system generates models in model spaces rotated by an equivalent angle.

It will further be appreciated that although in the above described embodiments a particular pattern of calibration markings has been described, in other embodiments other patterns could be used to determine the relative position and orientations of cameras of monitoring systems.

It will also be appreciated that although in the above described examples a calibration object in the form of a rectangular calibration plate 250 has been described, other forms of calibration object could be used. Thus for example, rather than being rectangular in shape the calibration object could comprise two planar areas bearing calibration markings connected by a rod where the rod acts to space the calibration areas by a fixed distance corresponding to the distance between a first and a second monitoring position such as the distance between a set up area and a treatment area or a treatment area and an imaging area.

In some embodiments a calibration object, such as the calibration plate 250, may be arranged to contain a set of radio opaque markers to assist with the identification of the relative positions of the monitoring system cameras 230-234; 380,386 and an irradiation position such as a treatment room iso-center 226; 392 or a fixed position 394 relative to an imaging apparatus.

In such embodiments in addition to being positioned and imaged as has been described in the previous embodiments the calibration object may additionally be irradiated by the treatment apparatus to obtain an irradiation image of the radio opaque markers located in the vicinity of the treatment room iso-center 226; 392. The obtained radiation images can then be analyzed to identify the correspondence between the positioning of the calibration object and the treatment room iso-center 226; 392. When calibrating the patient monitoring system 10 the identified position of the treatment room iso-center 226; 392 could be used to fix the co-ordinate system for the patient monitoring system 10 with the patient monitoring system 10 being arranged to generate models relative to the identified position and in a model space a fixed distance from that position. In this way, by providing a calibration object containing radio opaque markers, the patient monitoring system 10 can be calibrated more accurately to the treatment room iso-center 226; 392, as calibrating the system in this way avoids any errors arising due to potential inaccuracies with a laser highlighting system.

Although in the above described embodiments, a monitoring system involving stereoscopic cameras for monitoring a patient has been described as being calibrated, it will be appreciated that the described approach to calibrating a patient monitoring system is also generally applicable to other forms of patient monitoring systems including patient monitoring systems utilizing other forms of 3D cameras such as time of flight cameras and cameras based on the imaging of patterns of structured light projected on to a surface of an object to be modeled.

It should be noted that other types of calibration objects, than the one defined in the previous sections can also be used. That is, in an embodiment, the calibration plate may be an active calibration plate. The active calibration plate is defined as a calibration plate which is configured to illuminate actively, i.e. comprises illuminative markers thereon. The pattern of the calibration plate may be as described herein, however, other types of calibration patterns could be contemplated.

In the previous sections of the disclosure a plurality of embodiments has been described which relates to monitoring of patients being treated and/or scanned by a e.g. a bore based medical apparatus. Especially the embodiments described relates how to monitor, via a camera monitor system, the motion of the patient in a setup stage and the motion of a patient in e.g. a scanning and/or treatment stage. As previously mentioned, there is a tendency within the field of medical diagnostics and treatment to aim at optimizing the procedures concerning, scanning and treatment of e.g. a cancer patient. In that regard, as also mentioned in relation to FIGS. 12 to 18, there have been an aim to combine scanning modalities, such as CT and MR scanners with radiotherapy scanners, and thus a need for a camera monitoring system which enables monitoring of a patient, while the patient is positioned within a bore based medical apparatus. An example of such system was explained in relation to at least FIGS. 17 and 18 with the camera monitoring system and calibration methods as described throughout this disclosure.

However, in a further development of such systems, it is contemplated that the radiotherapy part of the medical apparatus forms an integrated part of the bore based imaging apparatus, such as a CT and/or MR scanner. In such cases, the couch need only to be positioned within the bore of the combined scanning and treatment bore based system. In such systems, which are illustrated schematically in FIGS. 19 to 22, there is a similar need to allow for patient monitoring as described herein.

Thus, embodiments of a camera monitoring system for a bore based medical apparatus, having both a scanning modality and a treatment modality integrated therein will now be described in more detail.

Figure 19:
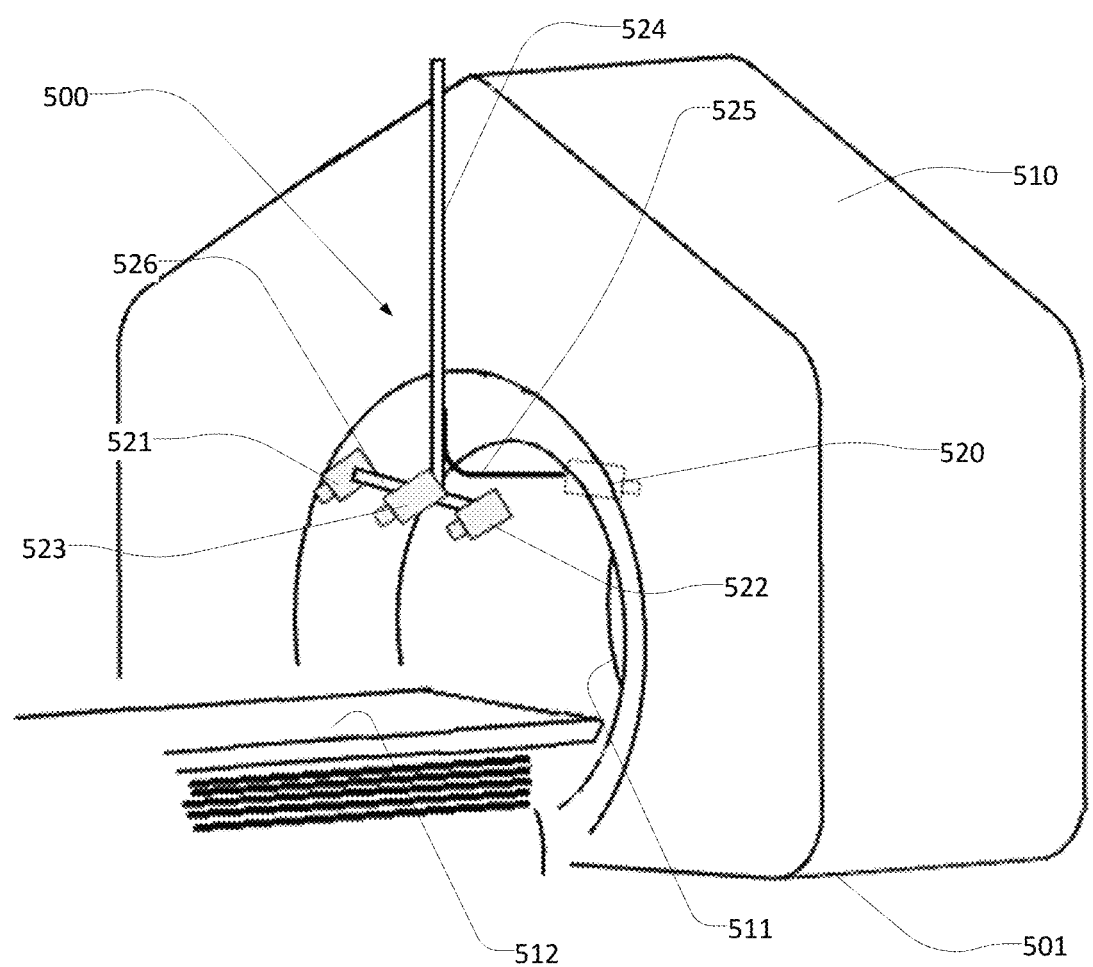
FIG. 19 illustrates an embodiment of a camera monitoring system mounted in relation to a bore based medical apparatus.

Referring to FIG. 19, a camera monitoring system of an embodiment is illustrated. The camera monitoring system is configured to be arranged in connection with a bore based medical apparatus 501, wherein the bore based medical apparatus 501 comprises an enclosure structure 510 having a bore 511 and enclosing a CT or MR imaging modality together with a radiotherapy radiation beam. The bore 511 of the enclosure structure 510 is configured to receive a couch 512, wherein during use a patient is to be positioned onto the couch 512.

As seen in the figure, the camera monitoring system 500 is configured to be arranged in connection with the enclosure structure and comprises in more detail at least one motion monitor camera 520 with a first field of view oriented in a direction inside the bore 511 and configured to record images of at least a target area of the patient during use of the medical apparatus, especially during radiotherapy. The motion monitor camera preferably extends a distance into the bore, and is thus illustrated in a dotted line to indicate that the motion monitor camera is substantially covered by the enclosure structure 510.

The camera monitoring system furthermore comprises at least one setup camera 522 oriented with a second field of view in a direction outside of the bore 511 and configured to record images of the patient during a positioning of the patient onto the couch 512. Both the motion 520 and setup 522 cameras are configured to be in data communication with at least one patient monitor processor 530, which patient monitor processor is configured to receive image data from each of the cameras. The motion monitor processor described in relation to this embodiment substantially corresponds to the computer 14 illustrated in relation to FIG. 2. The motion monitor processor is configured to i) process image data from the setup camera 522 in a setup stage, to generate a 3D surface model of the patient lying on the couch and to correlate the generated 3D model surface with a reference surface stored in the patient monitor processor, and subsequently to ii) process image data received from the motion monitor camera 520 in a monitoring stage to create time-dependent 3D surface models of said patient lying on the couch 512 and when said couch 512 is moved into the bore 511 of the medical apparatus. In this way, the patient monitor processor 530 is configured to track any movement of the time-dependent 3D surface model of the patient in relation to the reference surface, wherein a movement of the time-dependent 3D surface model in relation to said reference surface is output as a displacement value.

It should be noted that the figures illustrate at least two setup cameras 521, 522, however it will be understood that only one camera may be used for setting up the camera.

For all the embodiments described herein, it should be understood that in an embodiment the motion monitor processor is configured to output a displacement value. In the embodiments described herein it should be understood that one ore more displacement values could be output. This/these displacement value is/are configured to be compared to a set threshold value, wherein if the displacement value exceeds the set threshold, a displacement indicator is displayed to a clinician on e.g. a computer screen. This allows information to the clinician of a potential patient movement, which may have caused the target area for radiotherapy to be displaced in view of the focus of the radiation beam. In this way, the clinician is informed that the treatment potentially should be halted, and the patient repositioned.

In an alternative embodiment, the displacement value is configured to be compared to a set threshold value, wherein if the displacement value exceeds the set threshold, a control signal is sent to the medical apparatus, wherein the control signal is configured to halt the treatment or scanning process.

In a further embodiment, also illustrated in FIG. 19, the camera monitoring system may comprise at least one couch monitor camera 523 having a third field of view oriented in a direction towards an end of the couch and facing away from the bore 511. This allows for tracking of the movement of the couch, as described in previous embodiments of the disclosure. It should thus be noted that the couch monitoring camera illustrated in FIGS. 19 to 22 may be configured in correspondence with the couch monitoring camera described in relation to FIGS. 12 to 13 etc. A main difference is however, that in the embodiments of FIGS. 19 to 22, the couch monitoring camera and the setup cameras are configured to be directed with their respective field of views in a direction away from the bore 511. This is due to the fact, that the cameras in the FIGS. 19 to 22 are arranged differently on the enclosure structure than illustrated and described in FIGS. 12 to 13, etc. The principles of operation and function are however alike. By using the couch monitoring camera 523, it is possible to use a simplified calibration plate to calibrate the patient setup cameras 521, 522 and motion monitor camera 520. The couch monitor camera in conjunction with the calibration data at each location will determine a common calibration between the two groups of cameras as the offset between calibration plate locations will be known.

In alignment with the motion monitor camera 520 and the setup camera 521,522, the couch camera 523 is configured to transmit couch image data to the motion monitor processor, wherein the processor is configured to utilize the couch image data to evaluate a couch movement between the position of the couch in said setup stage and the position of the couch in said monitoring stage, as previously described.

In an embodiment, the motion monitor camera 520, and the setup cameras 521, 522 are configured as 3D stereovision camera systems, comprising a projector configured to project light onto the couch within the first and second field of views of the monitor and setup cameras, respectively, wherein the field of views at least are oriented to correlate with said target area of said patient. It should be noted, that other types of cameras could be used as previously mentioned.

In more detail, and as illustrated in FIG. 19, at least one motion monitor camera 520 is configured to be positioned on a camera mount 524 together with the at least one setup camera 521; 522. Thus, as can be seen in FIG. 19, the motion monitor camera 520 is positioned on a first branch 525 of the camera mount 524, which first branch 525 extends at least partly into the bore 511 of the medical apparatus.

Furthermore, the setup camera 521, 522 is in this embodiment configured to be arranged on a second branch 526 of the camera mount 524. In additional, the camera mount 524 may also be configured with the couch monitor camera 523, which couch monitoring camera 523 is also arranged onto the second branch 526. It should be noted that other suitable constructions could be used, and this is just provided as an example of how to arrange the camera monitoring system in relation to the bore based medical apparatus. The position of cameras 521, 522 can be within the body of the treatment system. Their position is such that any occlusions by the therapist setting up the patient for treatment will be minimized as the therapist body will not be blocking the view of the cameras, if they were, for example located in the ceiling looking down onto the patient.

Figure 20:
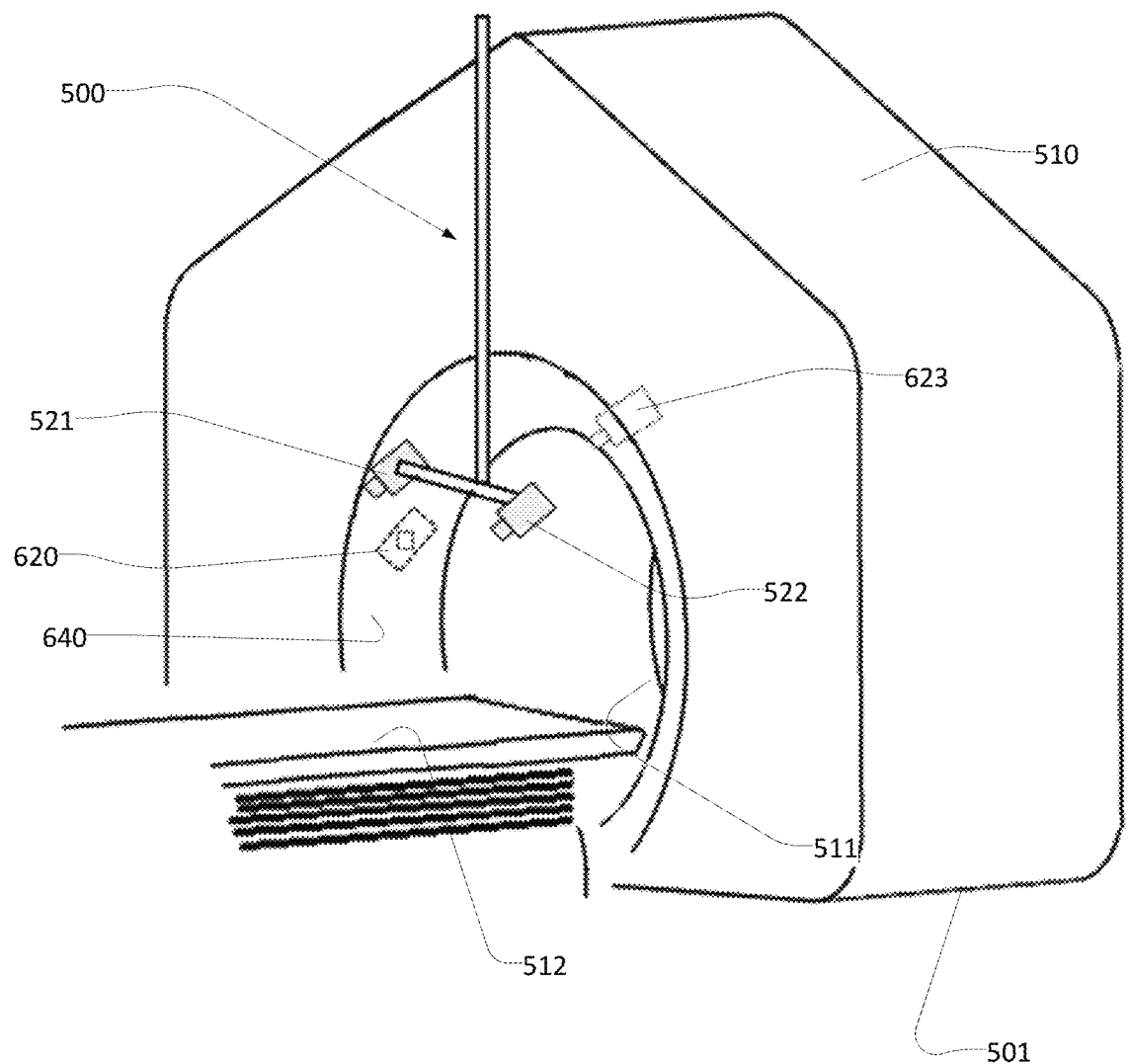
FIG. 20 illustrates an embodiment of a camera monitoring system in another setup in relation a bore based medical apparatus.

Referring now to FIG. 20 an embodiment of the camera monitoring system for a bore based medical apparatus 501 is illustrated. In this embodiment, the same type of cameras as previously described are also used. Thus, equal numbering will apply and only the differences will be explained in more detail. As illustrated in FIG. 20, the motion monitoring camera 620 is in this embodiment configured to be integrated into a part of an inside 640 of said bore 511. The integrated motion monitor camera 620 is arranged and positioned within the bore 511 with a field of view covering at least a target area of the patient.

Even though not illustrated in further detail, it should be understood that in an embodiment, the camera monitoring system may comprise at least two motion monitor cameras, wherein a first of said motion monitor camera 620 is configured to be integrated in a first side 640 of the bore 511 and the second of said motion monitor cameras (not illustrated) are configured to be integrated into a second side (not illustrated) of said bore 511. Thus, the first and second motion monitor cameras are configured as an integrated part of two opposing side surfaces of said enclosure structure and are oriented to share a common field of view correlating with said target area of said patient.

Figure 22:
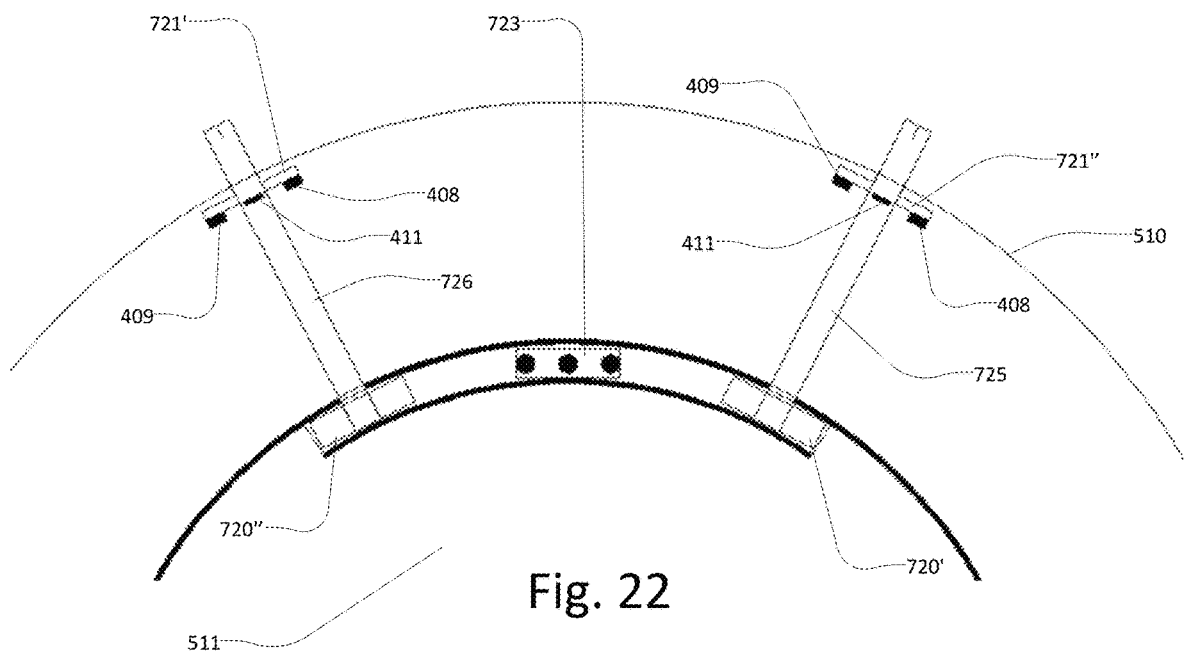
FIG. 22 illustrates a front view of a camera monitoring system in a setup in relation to a bore based medical apparatus.

Referring now to FIGS. 21 and 22 an exemplified illustration of the camera monitoring system being partly inserted into the bore of the bore based medical apparatus is illustrated. FIG. 21 illustrates a schematic side view of a bore based medical apparatus, wherein the couch 712 is positioned at least partly within the bore 711. As illustrated in the figure, the system is configured with a setup iso-center 751 and a treatment iso-center 752, to which the respective cameras are oriented. Thus, as illustrated, the setup camera 721 is configured so as to have a field of view covering at least the setup iso-center 751, whereas the motion monitor camera 720 is configured to cover at least the treatment iso-center. Especially the treatment room iso-center is of importance in view of ensuring that the patient does not move out of position of the focus of the radiation beam.

As further illustrated in FIG. 21, the camera monitoring system is connected with the bore based medical apparatus, in such way that the couch monitoring camera 723 is configured to cover a field of view covering a uniquely identifiable feature 760. Accordingly, in an embodiment the couch incorporates uniquely identifiable features, which may be tracked. An example of this may be a CCTV type camera mounted at the foot of the couch. A feature recognition algorithm can be used to detect the shape of the unique feature (possibly following a Hough transform being applied to the raw image), which has been trained on the feature. The Centre of Gravity of this feature is calculated, and using a pair of sensors in a calibrated camera the x,y and z coordinates can be calculated. By tracking this feature continuously, the movement/location of the couch may be determined.

In an alternative embodiment, the couch may be monitored by use of a marker positioned or arranged in connection with the couch. Thus, in an embodiment, illustrated in FIG. 21A, a marker 760 is located at the foot end of the couch and observed from the couch monitoring camera 723, located in front (alternatively above) the bore system. It should be understood that the couch 712 illustrated in FIG. 21A is inserted into the bore in a similar manner as illustrated in FIG. 21. Thus, the marker 750 is substantially positioned in the same end of the couch as the marker 760 shown in FIG. 21. The marker 750 may consist of one or more active emitters or retroreflective markers 750A, 750B, 750C. For full 3D marker tracking, preferably 3 markers may be used. This allows the couch position to be tracked and information on the patient position to be obtained during couch movement.

FIG. 22 illustrates a front view of the bore based medical apparatus as shown in FIG. 21. As illustrated in FIG. 22, the system may be configured with two motion monitor cameras 720', 720", which are configured to be integrated, or at least extending, into the bore based medical apparatus. It should be noted that the Figure illustrates the back side of the motion monitor cameras 720', 720" and thus contemplated that the cameras are imaging an object, e.g. a patient within the bore. The motion monitor cameras 720', 720" are mounted on a camera mount having a first branch 725 and a second branch 726. Each of these branches 725, 726 also comprises a setup camera 721', 721", which are positioned on the branch in such a manner that the field of view of the setup cameras is not obstructed by the motion monitor camera 720', 720". Thus, the motion monitor cameras 720', 720" are configured to cover a field of view containing the treatment iso-center and the setup cameras 721', 721" are configured to cover a setup iso-center without obstructing the field of view of the respective other cameras.

Furthermore, it should be understood that the branches 726, 725 are substantially in a mounted position on the bore based medical apparatus arranged to abut or at least follow the surface of the bore based medical apparatus enclosure structure.

Further embodiments includes:

Embodiment 1: A method of calibrating a patient monitoring system for monitoring the positioning of a patient in a first and a second location a fixed distance apart, the method comprising:
providing a monitoring system operable to obtain images of a patient in the vicinity of the first and second locations;
providing a calibration object, the calibration object bearing a first set of calibration markings and a second set of calibration markings, the first set of calibration markings being offset from the second set of calibration markings by a distance corresponding to the distance between the first and second locations;
positioning the calibration object so that the first calibration markings are located in the vicinity of the first location and the second set of calibration markings are located in the vicinity of the second location;
using the monitoring system to obtain images first and second set of calibration markings; and
calibrating the monitoring system on the basis of the obtained images.

Embodiment 2: A method in accordance with embodiment 1, wherein the monitoring system comprises a plurality of 3D cameras, wherein at least one 3D camera is arranged to obtain images of objects in the vicinity first location and at least one 3D camera is arranged to obtain images of objects in the vicinity of the second location.

Embodiment 3: A method in accordance with embodiment 2, wherein the 3D cameras comprise 3D cameras selected from the group comprising: stereoscopic cameras; 3D time of flight cameras and 3D cameras utilizing the projection of structured light onto the surface of an object being monitored.

Embodiment 4 A method in accordance with any preceding embodiments wherein the first set of calibration markings and second set of calibration markings comprise an array of circular markings wherein the circular markings in the array are located in known positions relative to one another.

Embodiment 5: A method in accordance with embodiment 4 wherein the calibration markings further comprise one or more lines arranged on the surface of the calibration object in a fixed relationship relative to the array of circular markings.

Embodiment 6: A method in accordance with any preceding embodiments, further comprising, utilizing a laser lighting system to highlight a position in space, wherein positioning the calibration object so that the first and second of calibration markings are located in the vicinity of the first location and the second set of calibration markings are located in the vicinity of the second location comprises aligning markings on the surface of the calibration object with light projected by the laser lighting system.

Embodiment 7: A method in accordance with embodiment 6, wherein the position in space highlighted by the laser lighting system comprises a position corresponding to a position selected from the group comprising: a treatment room iso-center of a radiotherapy treatment apparatus; a point identifying the center of a set up position for a patient undergoing radiotherapy treatment; and a point having a fixed relationship with an imaging apparatus for obtaining internal images of a patient undergoing radiotherapy treatment.

Embodiment 8: A method in accordance with any preceding embodiments wherein calibrating the monitoring system on the basis of the obtained images comprises processing the obtained images to determine the relative position and/or orientation of image planes of the obtained images of the positioned object relative to a point on the surface of the imaged calibration object.

Embodiment 9: A method in accordance with embodiment 8 wherein processing the obtained images to determine the position or orientation of image planes corresponding to the obtained images relative to the positioned calibration object comprises utilizing the obtained images to determine the position or orientation of image planes corresponding to the obtained images relative to a fixed point relative to calibration markings provided on the surface of the calibration object appearing in the obtained images.

Embodiment 10: A method in accordance with embodiment 9 wherein at least some of the calibration markings define points corresponding to corners on a square wherein processing the obtained images to determine the position or orientation of image planes corresponding to the obtained images relative to a fixed point relative to calibration markings provided on the surface of the calibration object appearing in the obtained images comprises utilizing the obtained images to determine the position or orientation of image planes corresponding to the obtained images relative to the center of the square identified by the calibration markings.

Embodiment 11: A method in accordance with any preceding embodiments wherein the calibration object contains a set of radio opaque markers, the method further comprising utilizing a treatment apparatus to irradiate the positioned calibration object to obtain an irradiation image of the calibration object; and analyzing the obtained image to determine the relative positioning of the calibration object relative to a treatment room iso-center.

Embodiment 12: A method in accordance with any preceding embodiments wherein calibrating the monitoring system on the basis of the obtained images comprises calibrating the monitoring system to generate models of objects observed in the vicinity of the first location in a first model space and to generate models of objects observed in the vicinity of the second location in a second model space wherein the first and second model spaces are offset by a vector corresponding the physical distance between the first and second locations.

Embodiment 13: A method in accordance with any preceding embodiments wherein calibrating the monitoring system on the basis of the obtained images comprises calibrating the monitoring system to generate models of objects observed in the vicinity of the first location in a first model space and to generate models of objects observed in the vicinity of the second location in a second model space wherein the first and second model spaces are rotated by an angle relative to one another.

Embodiment 14: A method in accordance any preceding embodiments wherein the calibration markings comprise an array of calibration markings and calibrating the monitoring system on the basis of the obtained images comprises utilizing obtained images of the array to identify lens distortions present in the obtained images on the basis of the appearance of the array in the obtained images.

Embodiment 15: A calibration object for calibrating a patient positioning monitor operable to monitor the positioning of a patient relative to a first position and a second position separated by a fixed physical distance, the calibration object comprising a first set of calibration markings and a second set of calibration markings positioned on the surface of the calibration object wherein the first and second set of physical markings have a fixed relationship between points on the surface of the calibration object physically separated from one another by a distance corresponding to the distance between the first position and the second position operable to be monitored by the patient positioning monitor.

Embodiment 16: A calibration object in accordance with embodiment 15 wherein the first set of calibration markings and second set of calibration markings are rotated relative to one another by an angle.

Embodiment 17: A calibration object in accordance with embodiment 16 wherein the radiation object contains a set of radio opaque markers It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A camera monitoring system for a bore based medical apparatus having at least one of an imaging apparatus configured to record diagnostic images of a patient and a treatment apparatus integrated into the bore based medical apparatus, the camera monitoring system comprising:
  one or more 3D cameras, each comprising:
    a first image sensor and a second image sensor mounted on a circuit board, wherein the first and second image sensors are mounted on opposing surfaces of the circuit board, the circuit board is contained within a housing which also contains a first mirror and a second mirror positioned within the housing wherein the first image sensor is presented with a first view of an object to be imaged via the first mirror and second image sensor is presented with a second view of an object to be imaged via the second mirror, and
    wherein the camera furthermore, comprises a projector configured to project light on the surface of an object to be imaged by the first and second image sensors,
    a first lens arrangement positioned between the first image sensor and the first mirror, wherein the first image sensor is presented with a first view of an object to be imaged via the first lens arrangement and the first mirror, and
    a second lens arrangement positioned between the second image sensor and the second mirror, wherein the second image sensor is presented with a second view of an object to be imaged via the second lens arrangement and the second mirror; and a processor configured to process images obtained by the image sensors of the one or more 3D cameras and to generate a 3D model of the surface of an imaged object, and wherein at least one of the more or more 3D cameras is configured to be integrated or extend into a bore of the bore based medical apparatus, where a camera field of view covers an internal part of the bore of the medical apparatus.

2. A camera monitoring system in accordance with claim 1, wherein the first and second lens arrangements extend along an axis which is substantially perpendicular to the surface of the circuit board.

3. A camera monitoring system in accordance with claim 2, wherein the circuit board, image sensors, lens arrangements and mirrors are contained within the housing.

4. A camera monitoring system in accordance with claim 3, wherein the first and second views of an object to be imaged correspond to image planes viewing the object to be imaged which lie outside of the housing containing the circuit board, image sensors, lens arrangements and mirrors.

5. A camera monitoring system in accordance with claim 1, wherein the first and second mirrors are angled relative to the surface of the circuit board at an angle of 45°.

6. A camera monitoring system in accordance with claim 1, wherein the one or more 3D cameras are configured to be inserted in a bore of the bore based medical apparatus along an inside top surface of the bore in such manner that a top portion of the camera is aligned with the inside top surface of the bore, wherein the camera is configured with the first mirror and the second mirror being angled in a direction downwards from the top portion of the camera towards the bottom portion of the camera, and wherein further the first and second mirror are angled inwards toward the center of the camera, wherein further, the first and second sensor are arranged in relation to the first and second mirror, so as to provide a substantially perpendicular view plane from the first and second mirror.

7. A camera monitoring system in accordance with claim 1, each of the one or more 3D cameras further comprising a third and a fourth image sensor wherein the third and fourth image sensors are mounted on opposing surfaces of the circuit board, and a third and a fourth mirror positioned within the housing so that the third image sensor is presented with a third view of an object to be imaged via the third mirror and the fourth image sensor is presented with a fourth view of an object to be imaged via the fourth mirror.

8. A camera monitoring system in accordance with claim 7, each of the one or more 3D cameras further comprising: a third lens arrangement positioned between the third image sensor and the third mirror, and a fourth lens arrangement positioned between the fourth image sensor and the fourth mirror, wherein the third image sensor is presented with a third view of an object to be imaged via the third lens arrangement and the third mirror and the fourth image sensor is presented with a fourth view of an object to be imaged via the fourth lens arrangement and the fourth mirror.

9. A camera monitoring system in accordance with claim 8, wherein the third and fourth mirrors are angled relative to the first and second mirrors.

10. A camera monitoring system in accordance with claim 9, wherein the first and third mirrors and the second and fourth mirrors are provided on the surface of a rhomboidal trapezium.

11. A camera monitoring system in accordance with claim 1, wherein the projector is a speckle projector and comprises a light source, a collimator, and a lens arrangement.

12. A camera monitoring system in accordance with claim 11, wherein the light source, the collimator and the lens arrangement are aligned along an axis which lies within a plane containing the circuit board.

13. A camera monitoring system in accordance with claim 1, wherein the first and second mirrors are angled relative to the surface of the circuit board at an angle of 43.5°.

14. A camera monitoring system in accordance with claim 2, wherein the first and second mirrors are angled relative to the surface of the circuit board at an angle of 45°.

15. A camera monitoring system in accordance with claim 2, wherein the first and second mirrors are angled relative to the surface of the circuit board at an angle of 43.5°.

16. A camera monitoring system in accordance with claim 3, wherein the first and second mirrors are angled relative to the surface of the circuit board at an angle of 45°.

17. A camera monitoring system in accordance with claim 4, wherein the first and second mirrors are angled relative to the surface of the circuit board at an angle of 45°.

* * * * *